United States Patent
Richards

(10) Patent No.: US 11,488,702 B2
(45) Date of Patent: *Nov. 1, 2022

(54) SYSTEM AND METHOD FOR IMPROVING CARDIOVASCULAR HEALTH OF HUMANS

(71) Applicant: PhysIQ, Inc., Naperville, IL (US)

(72) Inventor: Dylan Richards, Chicago, IL (US)

(73) Assignee: PhysIQ, Inc., Naperville, IL (US)

( * ) Notice: Subject to any disclaimer, the term of this patent is extended or adjusted under 35 U.S.C. 154(b) by 354 days.

This patent is subject to a terminal disclaimer.

(21) Appl. No.: 16/775,971

(22) Filed: Jan. 29, 2020

(65) Prior Publication Data

US 2021/0020293 A1    Jan. 21, 2021

Related U.S. Application Data

(63) Continuation of application No. 16/515,572, filed on Jul. 18, 2019, now Pat. No. 10,586,619.

(51) Int. Cl.
*G16H 20/30* (2018.01)
*G06N 3/08* (2006.01)

(52) U.S. Cl.
CPC .............. *G16H 20/30* (2018.01); *G06N 3/08* (2013.01)

(58) Field of Classification Search
CPC .................................. G16H 20/30; G06N 3/08
See application file for complete search history.

(56) References Cited

U.S. PATENT DOCUMENTS

| 9,693,727 | B1 | 7/2017 | Saalasti | |
|---|---|---|---|---|
| 10,586,619 | B1 | 3/2020 | Richards | |
| 2005/0236004 | A1* | 10/2005 | Magnuson | G16H 50/50 128/898 |
| 2014/0304204 | A1* | 10/2014 | Cameron | G06N 3/08 706/21 |
| 2019/0236447 | A1* | 8/2019 | Cohen | G06N 5/02 |

OTHER PUBLICATIONS

E. Baralis et al., "Predicting Cardiopulmonary Response to Incremental Exercise Test," 2015 IEEE 28th International Symposium on Computer-Based Medical Systems, 2015, pp. 135-140, doi: 10.1109/CBMS.2015.60. (Year: 2015).*
International Patent Application No. PCT/US2020/041611, International Search Report and the Written Opinion of the International Searching Authority, dated Aug. 5, 2020, 7 pages.
Abut, F., & Akay, M. F. (2015). Machine learning and statistical methods for the prediction of maximal oxygen uptake: recent advances. Medical Devices: Evidence and Research, 8, 369-379. https://doi.org/10.2147/MDER.S57281.

(Continued)

*Primary Examiner* — Evangeline Barr
(74) *Attorney, Agent, or Firm* — Fitch, Even, Tabin & Flannery LLP

(57) ABSTRACT

An estimate of a functional capacity such as VO2Max is made by applying the vital signs of a monitored human to a trained encoding neural network producing a cardio profile vector. The vector is applied to a trained functional capacity (VO2Max) neural network to estimate the functional capacity. Once estimated, an action is taken.

38 Claims, 16 Drawing Sheets

(56) References Cited

OTHER PUBLICATIONS

Altini, M. (2015). Personalization of energy expenditure and cardiorespiratory fitness estimation using wearable sensors in supervised and unsupervised free-living conditions. Eindhoven University of Technology. 243 pages. Retrieved from https://www.researchgate.net/publication/287204378.

Altini, M., Casale, P., Penders, J., & Amft, O. (2015). Personalized cardiorespiratory fitness and energy expenditure estimation using hierarchical Bayesian models. Journal of Biomedical Informatics, 56, 195-204. https://doi.org/10.1016/j.jbi.2015.06.008.

Altini, M., Casale, P., Penders, J., & Amft, O. (2016). Cardiorespiratory fitness estimation in free-living using wearable sensors. Artificial Intelligence in Medicine, 68, 37-46. https://doi.org/10.1016/j.artmed.2016.02.002.

Altini, M., Penders, J., Vullers, R., & Amft, O. (2014). Automatic Heart Rate Normalization for Accurate Energy Expenditure Estimation. Methods of Information in Medicine, 53(5), 382-388. https://doi.org/10.3414/ME13-02-0031.

Altini, M., Van Hoof, C., & Amft, O. (2017). Relation Between Estimated Cardiorespiratory Fitness and Running Performance in Free-Living: an analysis of HRV4Training data. 2017 IEEE EMBS International Conference on Biomedical and Health Informatics, BHI 2017, (January), 249-252. https://doi.org/10.1109/BHI.2017.7897252.

Baig, D.-Z. (2014). Physiological Control of Human Heart Rate and Oxygen Consumption during Rhythmic Exercises. 137 pages. Retrieved from http://arxiv.org/abs/1403.7105.

Cao, Z., Nobuyuki, M., Higuchi, M., Miyachi, M., Ishikawa-Takata, K., & Tabata, I. (2009). Predicting Vo2max with an Objectively Measured Physical Activity in Japanese Women. Medicine and Science in Sports and Exercise, 179-186. https://doi.org/10.1249/MSS.0b013e3181af238d.

Cheng, Jui-Chuan, et al., "Training and Evaluation of Human Cardiorespiratory Endurance Based on a Fuzzy Algorithm." International Journal of Environmental Research and Public Health, 2019, 16, 2390, 20 pages.

De Brabandere, B., Jia, X., Tuytelaars, T., & Van Gool, L. (2016). Dynamic Filter Networks, 1-14. Retrieved from https://arxiv.org/abs/1605.09673.

Edwards, H., & Storkey, A. (2017). Towards a Neural Statistician, 1-13. Retrieved from http://arxiv.org/abs/1606.02185.

Eslami, S. M. A., Rezende, D. J., Besse, F., Viola, F., Morcos, A. S., Garnelo, M., . . . Hassabis, D. (n.d.). Neural Scene Representation and Rendering, (i). 57 pages, https://doi.org/10.1126/science.aar6170.

Firstbeat Technologies Ltd. (2014). Automated Fitness Level (VO2max) Estimation with Heart Rate and Speed Data, 1-9. https://assets.firstbeat.com/firstbeat/uploads/2017/06/white_paper_VO2max_30.6.2 017.pdf.

Garnelo, M., Rosenbaum, D., Maddison, C. J., Ramalho, T Saxton, D., Shanahan, M., . . . Eslami, S. M. A. (2018). Conditional Neural Processes. 10 pages. Retrieved from https://arxiv.org/abs/1807.01613.

Garnelo, M., Schwarz, J., Rosenbaum, D., Viola, F., Rezende, D. J., Eslami, S. M. A., & Teh, Y. W. (2018). Neural Processes. 11 pages. Retrieved from https://arxiv.org/abs/1807.01622.

Gong, J., Qiu, X., Chen, X., Liang, D., & Huang, X. (2018). Convolutional Interaction Network for Natural Language Inference. Proceedings of the 2018 Conference on Empirical Methods in Natural Language Processing (EMNLP 2018), 1576-1585. Retrieved from http://www.aclweb.org/anthology/D18-1186.

Ha, D., Dai, A., & Le, Q. V. (2016). HyperNetworks, 1-29. Retrieved from http://arxiv.org/abs/1609.09106.

Hewitt, L. B., Nye, M. I., Gane, A., Jaakkola, T & Tenenbaum, J. B. (2018). The Variational Homoencoder: Learning to learn high capacity generative models from few examples. 10 pages. Retrieved from http://arxiv.org/abs/1807.08919.

Hunt, K. J., Fankhauser, S. E., & Saengsuwan, J. (2015). Identification of heart rate dynamics during moderate-to-vigorous treadmill exercise. BioMedical Engineering Online, 14(1), 1-13. https://doi.org/10.1186/s12938-015-0112-7.

Jia, N., Chen, X., Yu, L., Wang, R., Yang, K., & Luo, X. (2017). An Exercise Health Simulation Method Based on Integrated Human Thermophysiological Model. 15 pages, https://doi.org/10.1155/2017/9073706.

Kaiser, L., Gomez, A. N., & Chollet, F. (2017). Depthwise Separable Convolutions for Neural Machine Translation, 1-10. Retrieved from https://arxiv.org/abs/1706.03059.

Kim, Z. M., Oh, H., Kim, H.-G., Lim, C.-G., Oh, K.-J., & Choi, H.-J. (2017). Modeling long-term human activeness using recurrent neural networks for biometric data. BMC Medical Informatics and Decision Making, 17(S1), 57. 15 pages, https://doi.org/10.1186/s12911-017-0453-1.

Lee, J., Bahri, Y., Novak, R., Schoenholz, S. S., Pennington, J., & Sohl-Dickstein, J. (2018). Deep Neural Networks as Gaussian Processes, 1-17. Retrieved from https://arxiv.org/abs/1711.00165.

Malek, M. H., Housh, T. J., Berger, D. E., Coburn, J. W., & Beck, T. W. (2005). A New Non-Exercise-Based VO2Max Prediction Equation for Aerobically Trained Men. Journal of Strength and Conditioning Research, 19(3), 559-565. Retrieved from http://www.unm.edu/~rrobergs/478VO2maxEstimationMen.pdf.

Nes, B. M., Janszky, I., Vatten, L. J., Nilsen, T. I. L., Aspenes, S. T., & Wisløff, U. (2011). Estimating V̇O2peakfrom a nonexercise prediction model: The HUNT Study, Norway. Medicine and Science in Sports and Exercise, 43(11), 1-20. https://doi.org/10.1249/MSS.0b013e31821d3f6f.

Peters, M. E., Neumann, M., Iyyer, M., Gardner, M., Clark, C., Lee, K., & Zettlemoyer, L. (2018). Deep contextualized word representations, 15 pages. https://doi.org/10.18653/v1/N18-1202.

Plasqui, G., & Westerterp, K. R. (2006). Accelerometry and Heart Rate as a Measure of Physical Fitness: Cross-Validation. Medicine and Science in Sports and Exercise, 38(8), 1510-1514. https://doi.org/10.1249/01.mss.0000228942.55152.84.

Ruder, S. (2017). An Overview of Multi-Task Learning in Deep Neural Networks, 1-14. Retrieved from https://arxiv.org/abs/1706.05098.

Shen, D., Min, M. R., Li, Y., & Carin, L. (2018). Learning Context-Sensitive Convolutional Filters for Text Processing. 10 pages. Retrieved from https://www.aclweb.org/anthology/D18-1210.

Silva, G., Oliveira, N. L., Aires, L., Mota, J., Oliveira, J., & Ribeiro, J. C. (2012). Calculation and validation of models for estimating VO 2max from the 20-m shuttle run test in children and adolescents. Archives of Exercise in Health and Disease, 145-152. Retrieved from https://www.researchgate.net/publication/230560908.

Su, S. W., Chen, W., Liu, D., Fang, Y, Kuang, W., Yu, X., . . . Nguyen, H. T. (2010). Dynamic Modelling of Heart Rate Response Under Different Exercise Intensity. The Open Medical Informatics Journal, 4, 81-85. https://doi.org/10.2174/1874431101004020081.

Su, S. W., Wang, L., Celler, B. G., Savkin, A. V., & Guo, Y. (2006). Modelling and Control for Heart Rate Regulation during Treadmill Exercise. Conference Proceedings : . . . Annual International Conference of the IEEE Engineering in Medicine and Biology Society. IEEE Engineering in Medicine and Biology Society. Conference, 1, 4299-4302. https://doi.org/10.1109/IEMBS.2006.260573.

Swain, D. P, Parrott, J. A., Bennett, A. R., Branch, J. D., & Dowling, E. A. (2004). Validation of a New Method for Estimating VO2max Based on VO2 Reserve. Medicine and Science in Sports and Exercise, (14), 1421-1426. https://doi.org/10.1249/01.MSS.0000135774.28494.19.

Tönis, T. M., Gorter, K., Vollenbroek-Hutten, M. M. R., & Hermens, H. (2012). Comparing VO2max determined by using the relation between heart rate and accelerometry with submaximal estimated VO2max. Journal of Sports Medicine and Physical Fitness, 52(4), 337-343. Retrieved from https://www.researchgate.net/publication/230564759.

(56) References Cited

OTHER PUBLICATIONS

Van den Oord, A., Kalchbrenner, N., Vinyals, O., Espeholt, L., Graves, A., & Kavukcuoglu, K. (2016). Conditional Image Generation with PixelCNN Decoders, 1-13. Retrieved from https://arxiv.org/abs/1606.05328.

Wu, F., Fan, A., Baevski, A., Dauphin, Y. N., & Auli, M. (2019). Pay Less Attention With Lightweight and Dynamic Convolutions, 1-14. Retrieved from https://arxiv.org/abs/1901.10430v2.

* cited by examiner

SYSTEM AND METHOD FOR IMPROVING CARDIOVASCULAR HEALTH OF HUMANS

CROSS-REFERENCE TO RELATED APPLICATION

The present application is a continuation of and claims the benefit of U.S. application Ser. No. 16/515,572, filed on Jul. 18, 2019, which is incorporated herein by reference in its entirety.

TECHNICAL FIELD

This disclosure relates to performing actions that treat medical conditions and improve the health of humans, and, more specifically, determining these actions from an analysis of data obtained from humans.

BACKGROUND

There are numerous circumstances in the medical arts where it is highly valuable to determine the comparative health of an individual at a point in time, compared to others (or compared to known categories), or compared to the individual's history. In particular, this health determination often seeks to measure the individual's cardiopulmonary function, as blood circulation and gas exchange are front-line life-enabling in comparison to dietary metabolism or cognitive functions. In some aspects and as used herein, "health" refers to the cardiopulmonary vitality for humans although it will be understood that other types of health vitalities are possible.

Determining the comparative health of a human is useful in a variety of different ways. For example, these determinations can be used to determine the efficacy/side effects of a drug in a drug trial (e.g., whether the drug usage is improving the subject's health, sustaining the subject's health in view of expected degradation, or is having negative side effects on the subject's health). Comparative health determinations can also be used to obtain the efficacy of a device/procedure intervention in a clinical trial, or determine a capacity for treatment (e.g., in oncology treatments/chemotherapy, determine whether the patient sufficiently recovered from last treatment to endure more, whether the patient is being overtreated, or whether the treatment is otherwise harming the patient). These determinations can further be used in health care surveillance (e.g., tracking the day-over-day trajectory of a patient with chronic disease (e.g., heart failure or COPD), or post-surgical discharge). These determinations can additionally be used to identify individuals with undiagnosed disease in the population, or to enable early intervention (e.g., NYHA Class I Heart Failure, which is often underdiagnosed and is asymptomatic). Still further, these determinations can be used to evaluate the effectiveness of rehabilitative regimen (e.g., whether the regimen is helping the patient or whether the patient performing the regimen). Other examples are possible.

Indicators of health status are typically measured under "effort challenge" activities (activities that individuals may be reluctant to perform), such as exercise tests. In general, exercise tolerance is determined by three factors: pulmonary gas exchange; cardiovascular performance, including the peripheral vascular tree; and skeletal muscle metabolism. Methods for directly and objectively measuring an individual's cardiopulmonary functional capacity are generally invasive or arduous to set up and perform. Because of expense or inconvenience, they are not easily deployed for long-term surveillance or repeated measurement, whether in a clinical trial or for extended monitoring of a patient.

For example, objective measurements of cardiopulmonary function include ventilatory anaerobic threshold (VAT) tests. VAT measurements involve successive blood samples are drawn from a subject during exercise challenge to determine an inflection point at which metabolism moves from aerobic to anaerobic. This method involves challenges of sequential blood gas testing and setup to acquire blood samples in an exercise equipment setting.

Another objective measurement of cardiopulmonary function includes the cardiopulmonary exercise test (CPET), where the subject is fitted with a breathing mask for measuring oxygen uptake and carbon dioxide production. The mask and connected equipment are able to measure O2 (and/or CO2) content from the breath, so that an objective estimate of oxygen uptake can be made, in particular as the subject reaches a plateau of maximum exercise capacity. This method requires specialty equipment as well as a laboratory-type exercise equipment setting.

Still another objective measurement of cardiopulmonary function includes the pulmonary function test (PFT), which uses either a spirometer or a plethysmograph chamber, to measure volumes and rates of air during breathing. This method only measures breathing, and so does not capture the "cardio" side of the health assessment. Nonetheless, it presents a way for objectively measuring structural gas exchange volume and flow.

Yet another objective measurement of cardiopulmonary function includes the cardiac echo doppler test, which is a measure of the cardiac output, physical distension and valve health of a person. These measurements are not expected to change much over short periods (weeks) of time. This measurement does not address the pulmonary side of performance or skeletal muscle metabolic health.

As a substitute for these objective measurements, more easily deployed tests like the "6-minute walk test" (6MWT) are used in health monitoring and clinical studies. In the 6MWT, a clinician marks out a stretch of hallway in which the tested individual walks back and forth as far as possible in 6 minutes. The distance walked is a proxy for cardiopulmonary exercise capacity. One problem with the 6MWT is its crudeness: Settings may vary in terms of obstacles or distractions; a tested individual may walk less distance owing to something other than cardiopulmonary fitness, such as arthritis, a headache, balance issues or joint pain. Hence results are noisy and only coarsely correlated to true health. Moreover, it is inconvenient for a tested individual to travel to the clinician's location to participate in the test.

Estimators of VO2Max have been derived based on physical attribute values such as age or gender. However, these are also only coarsely accurate, and of course lend no information on day-over-day changes in the performance of an individual. For example, such estimators are useless for monitoring the status of a patient with chronic disease who may evolve a disease exacerbation over days or weeks. More recently, VO2Max estimators have begun to be developed using features from fitness trackers, mainly heart rate, in combination with physical attribute values, but these have lacked accuracy, and often still require the subject to perform a specific exercise routine during which the assessment is made.

BRIEF DESCRIPTION OF THE DRAWINGS

For a more complete understanding of the disclosure, reference should be made to the following detailed description and accompanying drawings wherein.

DETAILED DESCRIPTION

Figure 1:
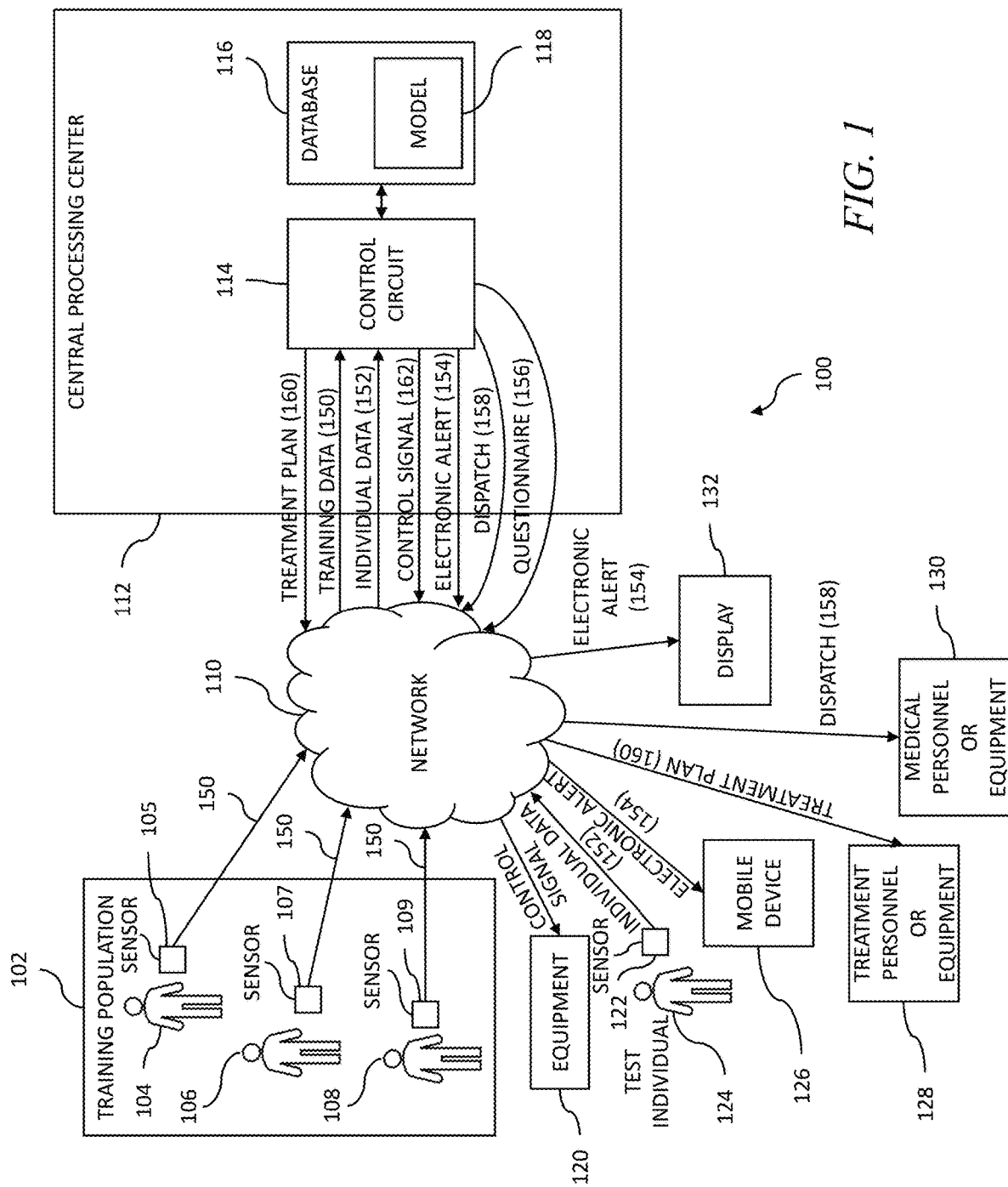
FIG. 1 comprises a diagram of a system as configured in accordance with various embodiments of these teachings.

Generally speaking, the invention relates to machine learning-based computational systems and methods that obtain and later utilize wearable sensor data from an individual engaged in ambulatory activities (e.g., activities that involve movement) or other activities of daily living. After obtaining the data, the approaches described herein generate one or more of: an estimated VO2Max (maximal oxygen uptake); a category or diagnosis of health or medical condition (e.g., selected from a range, such as normal, pre-heart failure, heart failure (HF) Class I, HF Class II, HF Class III, HF Class IV), an estimated performance capacity on an idealized activity such as a 6-minute walk test (6MWT); or a day-over-day index of worsening or improving cardiopulmonary health. Other examples are possible.

In one example, a chest-adhesive wearable patch is secured to a human user and obtains electrocardiogram ("ECG") and 3-axis accelerometer ("XYZ") waveform data, and vital sign data is obtained from the sensor data. The vital sign data may include, in examples, one-minute averaged activity (e.g., gross accelerometer RMS over last moving window of two minutes), one-minute averaged heart rate (HR), and (optionally) one-minute averaged respiration rate (RR). Other examples are possible. To take one example, an input to the approaches described herein is 1,440 minutes of data (or a substantial subset thereof), comprising one day. However, in other examples, this could be two days or multiples of days. Other time windows may also be used.

The present approaches create, train, and utilize mathematical models in the form of neural networks (e.g., convolutional neural networks (CNNs)). Once created and trained, data from an individual human is selectively applied to the models to obtain an output. In one example, the output is an estimated VO2Max for the individual.

The output can be used in various ways. For example, the output of an estimated VO2Max, category, idealized exercise capacity metric (6MWT) or the like can be used by a medical clinician to assess either the trend in the individual's health over time (e.g., a heart failure patient being monitored at home after a recent discharge from hospital) or diagnose the stage of an individual's progressive disease. The output can be used to control medical equipment, for example, adjust the drip rate of an intravenous (IV) machine. Alert messages can also be sent to patients. Additionally, medical personnel can be directed to and navigate to patients to provide assistance.

In other examples, the output of the approaches provided herein is used in a clinical trial, as a measure of effectiveness on cardiopulmonary health of a drug, device or procedure as between a test group of humans and a control group of humans. The output of the present approaches may also be tracked for negative side-effects of same.

In aspects, the present approaches leverage the dynamics of vital signs over a time period (e.g., a day, at least one diurnal cycle) to determine the measure of health of a subject. Information is garnered indirectly from the patterns of activity and vital sign responses, such as the lag between activity start or cessation and heart rate rise or return to baseline, respectively. These dynamics latently encode the functional capacity of the subject, without requiring the subject to engage in any specific activity or activity level or other prescribed exercise test. The present approaches harvest that latently encoded information to produce an objective measure of health.

In other aspects, the approaches described herein employ Artificial Intelligence techniques to train deep neural networks. The network architecture described herein provides benefits by not overfitting daily training data, and, at the same time, it does not require a tremendous amounts of labeled training data to be effectively trained.

Advantageously, the approaches provided herein make an accurate characterization of cardiopulmonary exercise capacity on an ongoing basis and are tailored to the individual, i.e., based on real-time measurements from the individual, without the inconvenience of existing or invasive tests. Using sensor data from wearables, these characterizations are accurately determined. In aspects and from various exertions throughout the day, activity and vital sign response (e.g., heart rate recovery after climbing stairs) encode hints, indicia, or tell-tale signs of the underlying functional capacity of the individual that day.

Ideally, the determined metric is generated (a) irrespective of reliance on the tested individual to perform a prescribed activity and (b) can be harvested from the normal backdrop of daily activities.

The present approaches train neural networks from wearable sensor data, yet do not require such extraordinary numbers of VO2Max results. The approaches provide health status indicators such as VO2Max, and 6MWT, which are recognizable and actionable by both humans (e.g., clinicians) and machines.

Advantageously, the present approaches provide a "fingerprint"-like cardio profile vector for an individual as expressed in a day of vital sign data. This fingerprint encapsulates the essential cardiopulmonary behavior of the individual expressed in their activities of daily living (ADLs).

With the present approaches, there is no need to force an individual to perform any particular activities every day. The cardio profile is captured based on their ADLs without constraint. This has the benefit of achieving higher compliance, and avoiding the problem that human subjects do not perform a prescribed set of activities reliably.

Furthermore, the present approaches produce significant savings on training data needed, by virtue of using easily collected vital sign data to train a network to generate the cardio profile, and then regressing that separately against a substantially smaller set of VO2Max (or other end assessment) results, which may be too expensive or hard to acquire in sufficient quantities for normal direct neural network training.

With the present approaches, regression of the cardio profile against a known, objective metric of cardiopulmonary health to provide an estimate of that metric continuously greatly enhances visibility into the subject's ongoing condition over time. It makes the health of the subject very interpretable to the clinician, by putting the output of the assessment in terms of a known metric.

Advantageously, the regressed metric, such as VO2Max, when tracked over time can show the directionality of the subject's health, just by observing the vital sign responses of the subject to ADLs.

Additionally, the regression metric like estimated VO2Max can replace noisier and less reliable tests like the 6MWT used in clinical trials and in clinical health assessments. Because the accuracy of the assessment according to the invention is better than coarse tests like 6MWT, it is possible that the clinical study can be reduced in size or come to conclusion more quickly because the statistics needed to achieve a similar power are smaller when the accuracy of the metric is tighter.

As explained elsewhere herein, the generation of a cardio profile vector allows for direct comparisons between populations of tested subjects that have high variability of personal health status and activities of daily living. With a 100-element vector, a variety of classifications can be achieved, and individuals can even be grouped by self-organizing clusters to uncover unforeseen commonalities between sub-populations.

In many of these embodiments, approaches for treating and improving the cardiopulmonary health of humans are provided. In an embodiment of the invention, an encoding neural network is configured to accept as input a time series duration (e.g., a day) of values for a selected plurality of cardiopulmonary variables from a subject, and to generate a multi-element cardio profile vector for that subject. A function generator neural network is configured to generate values for neural network connection weights for use in another network, when supplied with the cardio profile vector as input. An estimation neural network is configured to accept as input another time series duration of values for a subset of the selected plurality of cardiopulmonary variables from the subject. The subset omits at least one excluded variable, and the estimation neural network is configured to generate an estimate of the at least one excluded variable. The estimation neural network is configured using the weights output by the function generator network as weights of connections between nodes in the estimation neural network.

Iterative training in tandem and by a plurality of iterations is performed on the encoding neural network to produce a trained encoding neural network and on the function generator neural network to produce a trained function generator neural network. The training uses an error metric inclusive of the difference between the at least one excluded variable and the estimate of the at least one excluded variable generated by the estimation neural network.

For each of the iterations, a first duration of training data comprising a substantially contiguous time series of the selected plurality of cardiopulmonary variables from a training human subject is input to the encoding neural network. For each of the iterations, a second duration of the training data, substantially nonoverlapping in time with the first duration, comprises a substantially contiguous time series of the selected plurality of cardiopulmonary variables from the training human subject, and provides input to the estimation neural network. The estimation neural network provides the estimate of the at least one excluded variable. Time series durations of data from one or more training human subjects may be used for training. Once trained, the encoding neural network can be used to generate a cardio profile vector for any new human subject (e.g., a subject who may not be any of those human subjects used for training).

A functional capacity estimator is configured to accept as input a cardio profile vector generated by the trained encoding neural network for a human subject. The cardio profile vector may be augmented with a preselected set of physical attribute values of the human subject, and the functional capacity estimator outputs an estimate of a metric of functional capacity of the human subject.

The functional capacity estimator is trained using a plurality of matched examples to produce a trained functional capacity estimator. Each of the matched examples comprises a cardio profile vector, in some embodiments augmented with the physical attribute values from a person, matched with a corresponding measured functional capacity metric of that person, to enable regression of an input of a physical attribute-augmented cardio profile vector to an estimate of the metric of functional capacity.

The trained encoding neural network and the trained functional capacity estimator are deployed to accept as input a duration of monitored data from a monitored human subject. The monitored data comprises substantially contiguous time series of the selected plurality of cardiopulmonary variables. The trained encoding neural network generates a current cardio profile vector for the monitored human subject. The current cardio profile vector may be augmented with physical attributes of the monitored human subject. The trained functional capacity estimator generates from application of the physical attribute-augmented current cardio profile vector to the trained functional capacity estimator a current estimate of the metric of functional capacity.

Based upon the current estimate of functional capacity, one or more actions are performed. In one example, the current estimate in a time series with prior estimates are displayed to a clinician for review of possible health changes in the monitored human subject. In other examples, the current estimate is compared to prior estimates and a test is performed for a change. An alert is triggered to a clinician to investigate the health of the monitored human if a change is detected.

In still other examples, the current estimate is compared to prior estimates and a test is performed for a change whereupon a questionnaire is sent to the monitored human subject. In yet other examples, the current estimate is compared to prior estimates and a test is performed to detect a change whereupon an entry is made in the medical record of the monitored human subject indicating a change in health of the monitored human subject occurred.

In further examples, the current estimate is compared to estimates from other monitored human subjects, in order to quantify health affects between at least a control group receiving a first intervention and a test group receiving a second intervention in a clinical trial. In still other examples, the operation of a medical device is controlled or a parameter of the medical device is set where the medical device is associated with treating or monitoring the monitored human subject.

In aspects, the functional capacity is VO2Max. Other examples are possible.

In other aspects, the time series of selected plurality of cardiopulmonary variables is obtained by sensors that are non-invasively secured to the skin of the humans. In other examples, the time series of selected plurality of cardiopulmonary variables is obtained by sensors such as a camera, an electrocardiographic sensor, a light sensor, an accelerometer, an RF energy sensor, a temperature sensor, and a gyroscopic sensor. Other examples are possible.

In still other examples, the functional capacity estimator generates the current estimate of the metric of functional capacity using one of: a linear regression technique, a decision tree, a random forest estimation, or a gradient boosting model. In yet other examples, the functional capacity estimator comprises an estimation neural network. Other examples are possible.

In aspects, the cardiopulmonary variables comprise one or more of: a heart rate, a measure of physical activity or motion, a time domain heart rate variability, a respiration rate, a tilt angle, an A-fib probability, and a sample time difference. Other examples are possible.

In still other aspects, the current cardio profile vector comprises a plurality of real numbers, each of the real numbers associate with one or more of the cardiopulmonary variables.

In others of these embodiments, a system that is configured to treat and improve the cardiopulmonary health of humans includes a sensor and control circuit. The sensor is configured to obtain a duration of monitored data from a monitored human subject, comprising substantially contiguous time series of a selected plurality of cardiopulmonary variables, the sensor being deployed with a monitored human subject.

The control circuit is coupled to the sensor and is configured to: receive the duration of monitored data; apply the duration of monitored data to a trained encoding neural network and responsively create a current cardio profile vector for the monitored human subject; augment the current cardio profile vector as needed with physical attributes of the monitored human subject, and generate from the physical attribute-augmented current cardio profile vector a current estimate of the metric of functional capacity by applying the physical attribute-augmented current cardio profile vector to a trained functional capacity estimation neural network.

The trained functional capacity estimation neural network is created using a plurality of matched examples to produce the trained functional capacity estimation neural network. Each of the matched examples comprises a cardio profile vector, augmented with the physical attribute values from a person, matched with a corresponding measured functional capacity metric of that person, to enable regression of an input of a physical attribute-augmented cardio profile vector to an estimate of the metric of functional capacity.

Based upon the current estimate of functional capacity, one or more actions are performed. These actions include the control circuit rendering a display on a display screen of the current estimate in a time series with prior estimates to a clinician for review of possible health changes in the monitored human subject; the control circuit comparing the current estimate to prior estimates and testing for a change whereupon an electronic alert is triggered and transmitted to a clinician to investigate the health of the monitored human; the control circuit comparing the current estimate to prior estimates and testing for a change whereupon the control circuit transmits an electronic questionnaire to the monitored human subject; the control circuit comparing the current estimate to prior estimates and testing for a change whereupon the control circuit makes an entry in an electronic medical record of the monitored human subject indicating a change in health of the monitored human subject occurred; the control circuit comparing the current estimate to estimates from other monitored human subjects, in order to quantify health affects between at least a control group receiving a first intervention and a test group receiving a second intervention in a clinical trial; and the control circuit transmitting an electronic control signal that controls the operation or sets a parameter of a medical device associated with treating or monitoring the monitored human subject.

With respect to training, an encoding neural network is configured to accept as input a time series of a selected plurality of cardiopulmonary variables, and to generate a multi-element cardio profile vector. The function generator neural network is configured to generate weights when supplied with the cardio profile vector as input. The estimation neural network is configured to accept as input a time series of a subset of the selected plurality of cardiopulmonary variables, the subset omitting at least one excluded variable, and to generate an estimate of the at least one excluded variable. The estimation neural network is configured to use the weights output by the function generator network as weights of connections between nodes in the estimation neural network.

The encoding neural network and the function generator neural network are trained in tandem and by a plurality of iterations. The training of the encoding neural network produces the trained encoding neural network and the training of the function generator neural network produces a trained function generator neural network. The training of the encoding neural network and the function generator neural network uses an error metric inclusive of the difference between at least one excluded variable and the estimate of the at least one excluded variable generated by the estimation neural network. The estimation neural network is not itself trained, its weights being supplied dynamically by the function generator neural network with each set of inputs at the encoding neural network; the estimation network is however used to create the error metric. To further clarify, the weights of the estimation neural network are never truly "fixed" but vary with each set of input to the encoding neural network, and are determined dynamically by the function generator neural network, hence are not subject to training. Instead the function generator neural network is trained to be good at providing effective weights for use by the estimation neural network. In contrast, the weights of the encoding neural network and the function generator neural network remain "fixed" regardless of the input data, except when changed by the training process.

Training a neural network, as known to those skilled in the art, involves two distinct phases. The first phase is the forward pass through the neural network, where the network parameters are frozen, an input is provided to the network, and the network produces an estimate of the target output value. The second phase, known as the backward pass through the neural network, involves calculating the amount of error between the estimate of the target value and the target value itself. The partial derivative of each network parameter with respect to the error is then calculated for each layer in the network (this process is known in the art as backpropagation of error). The neural network parameters are then updated by subtracting a small multiple of each respective parameter's partial derivative. This two-phase process is then repeated until the network has learned to accurately produce estimates of the target output.

For each of the iterations: a first duration of training data comprising a substantially contiguous time series of the selected plurality of cardiopulmonary variables from a training human subject is input to the encoding neural network; and a second duration of the training data, substantially nonoverlapping in time with the first duration (excluding at least one excluded variable), comprising a substantially contiguous time series of the selected plurality of cardiopulmonary variables from the training human subject, provides input to the estimation neural network. The estimation neural network provides the estimate of the at least one excluded variable.

In still others of these embodiments, a system that is configured to treat and improve the cardiopulmonary health of humans includes: an encoding neural network, the encoding neural network configured to accept as input a time series of a selected plurality of cardiopulmonary variables, and to generate a multi-element cardio profile vector; a function generator neural network, the function generator neural network being configured to generate weights when supplied with the cardio profile vector as input; an estimation neural network, the estimation neural network being configured to accept as input a time series of a subset of the selected plurality of cardiopulmonary variables, the subset omitting at least one excluded variable, and to generate an estimate of the at least one excluded variable, wherein the estimation neural network is configured using the weights output by the function generator network as weights of connections between nodes in the estimation neural network; and a control circuit.

The control circuit is configured to iteratively train in tandem and by a plurality of iterations (1) the encoding neural network to produce a trained encoding neural network and (2) the function generator neural network to produce a trained function generator neural network. The training uses an error metric inclusive of the difference between the at least one excluded variable and the estimate of the at least one excluded variable generated by the estimation neural network.

For each of the iterations, a first duration of training data comprising a substantially contiguous time series of the selected plurality of cardiopulmonary variables from a training human subject is input to the encoding neural network; and a second duration of the training data (excluding at least one excluded variable), substantially nonoverlapping in time with the first duration, comprising a substantially contiguous time series of the selected plurality of cardiopulmonary variables from the training human subject, provides input to the estimation neural network. The estimation neural network provides the estimate of the at least one excluded variable.

A functional capacity estimator is configured to accept as input a cardio profile vector generated by the trained encoding neural network. The cardio profile vector may be augmented with a preselected set of physical attribute values of a human subject, and to output an estimate of a metric of functional capacity.

The control circuit is further configured to train the functional capacity estimator using a plurality of matched examples to produce a trained functional capacity estimator, each of the matched examples comprising a cardio profile vector augmented with the physical attribute values from a person if any, matched with a corresponding measured functional capacity metric of that person, to enable regression of an input of a physical attribute-augmented cardio profile vector to an estimate of the metric of functional capacity.

The trained encoding neural network and the trained functional capacity estimator are deployed to accept as input a duration of monitored data from a monitored human subject, comprising substantially contiguous time series of the selected plurality of cardiopulmonary variables, generate a current cardio profile vector for the monitored human subject, augment the current cardio profile vector with physical attributes of the monitored human subject, and generate from the physical attribute-augmented current cardio profile vector a current estimate of the metric of functional capacity.

Based upon the current estimate of functional capacity, one or more actions are performed. The one or more actions include that: the control circuit renders a display on a display screen of the current estimate in a time series with prior estimates to a clinician for review of possible health changes in the monitored human subject; the control circuit compares the current estimate to prior estimates and tests for a change whereupon an electronic alert is triggered and transmitted to a clinician to investigate the health of the monitored human; the control circuit compares the current estimate to prior estimates and tests for a change whereupon the control circuit transmits an electronic questionnaire to the monitored human subject; the control circuit compares the current estimate to prior estimates and tests for a change whereupon the control circuit makes an entry in an electronic medical record of the monitored human subject indicating a change in health of the monitored human subject occurred; the control circuit compares the current estimate to estimates from other monitored human subjects, in order to quantify health affects between at least a control group receiving a first intervention and a test group receiving a second intervention in a clinical trial; and the control circuit transmits an electronic control signal that controls the operation or sets a parameter of a medical device associated with treating or monitoring the monitored human subject.

Referring now to FIG. 1, one example of a system 100 for determining estimates of patient-related cardiopulmonary values or functional capacities such as VO2Max is described. The system 100 includes a training population 102 of humans including a first human 104, a second human 106, and a third human 108. Associated with the first human 104 is a first sensor 105, with the second human 106 is a second sensor 107, and with the third human 108 is a third sensor 109. The sensors 105, 107, and 109 couple to an electronic network 110. The electronic network 110 is coupled to a central processing center 112. The central processing center includes a control circuit 114, a database 116 (including a mathematical model 118).

The network 110 is coupled to equipment 120, a fourth sensor 122 (associated with test or monitored human 124), a mobile electronic device 126, treatment personnel or equipment 128, medical personnel or equipment 130, and a display 132.

The training population 102 includes a plurality of humans. In the present example, only three humans 104, 106, 108 are shown but it will be appreciated that the training population will typically be in the hundreds, thousands, tens of thousands, or even millions of humans.

Each of the humans is associated with a sensor (in this case, sensors 105, 107, and 109). As provided, the sensors 105, 107, and 109 are configured to sense one or more vital signs (or other sensed value) from the humans 104, 106, and 108. In aspects, the cardiopulmonary status of an individual is represented in the various dynamics of their vital signs over a day of activities of daily living (ADLs). Examples of vital signs include heart rate (HR), heart rate variability (variance of HR in unit time) (HRV), respiration rate (RR), gross motion/exertion (Activity—from 3-axes accelerometer on-body) (ACT or XYZ), body torso tilt (angle/degrees relative to upright for example) (TILT), and the presence of A-Fib (flags when HR and HRV may not be typical) (AF or AFIB). Other examples are possible. In examples, the sensors obtain various types of physical signals (e.g., electrical signals, movement, or ECG) and these are converted to a vital sign either at the sensor or at some other location.

All of the above vital signs can be obtained continuously (or periodically) from the sensors 105, 107, 109. In one example, the sensors 105, 107, and 109 are an adhesive torso patch with one-lead ECG (two electrode, upper left chest typically) plus 3-axes accelerometer (capturing accelerometry reflecting breathing movement and exertion to move the torso, the main part of the body). In other aspects, the vital signs can be computed at high sample rate (HR once every beat; RR every 5 or 10 seconds, or TILT every second as examples) and averaged to some standard rate, e.g., once per minute. This may be performed at the sensors 105, 107, and 109 or at the control circuit 114.

The sensors 105, 107, and 109 can be placed at other locations besides the torso of the humans. For example, the sensors 105, 107, and 109 may be worn on the wrist, from which typically a pulse signal can be acquired optically, indicative of blood pumping action. Wrist devices also typically have accelerometers, though this reflects both major exertions of the body (arising, walking, running) as well as minor peripheral activities (raising the arm, hand motions). Respiration can be acquired from the pulse signal as an envelope and possibly also as respiratory sinus arrhythmia seen in the timing of the pulse peaks. Although the wrist location suffers from more motion and the pulse signal is more easily lost than a chest-based ECG, substantial tracts of good data are still collectible, given the sedentary lifestyle of many people.

If wrist sensors are used, the neural networks used in the models described herein would use inputs that include pulse rate, respiration rate, activity, sample time gap, pulse rate variability, and alternatively filtered versions thereof. Other examples are possible.

In one specific example, the data obtained from the training population 102 includes "Day 1" data and "Day 2" data. In one example, Day 1 data is from a first calendar date and Day 2 data is from a second calendar date. However, it will be appreciated that the start time of such days of data need can occur at times other than midnight, and the Day 1 and Day 2 data may overlap on the same calendar date such as when Day 1 overflows to the first portion of a calendar date and Day 2 starts on that calendar date.

In another example, Day 1 and Day 2 vital signs are each obtained across a 24-hour period at 1-minute sampling rate (1440 samples per day) from eight channels, each z-score-normalized across the training data. The eight channels are: low pass heart rate (e.g., the heart rate after passed through a low-pass filter); high pass heart rate (e.g., the heart rate after passed through a high-pass filter); time domain heart rate variability (e.g., HRV over a moving window of time); gross activity; respiration rate; tilt angle (e.g., from torso patch); A-Fib probability (e.g., 0-1 probability of A-Fib present in ECG); and sample time difference (e.g., which informs about gaps in data).

In yet another example, the Day 1 and Day 2 vital signs include low pass heart rate; high pass heart rate; time domain heart rate variability; gross activity; respiration rate; and tilt angle (e.g., from torso patch).

In another example, the Day 1 and Day 2 vital signals include heart rate; time domain heart rate variability; gross activity; respiration rate; and blood pressure (e.g., from a wrist worn device).

While the above-mentioned examples utilize one-minute averages of vital signs, other examples are possible. For example, a sampling rate from 15-second averaged vital sign values up to 5-minute averaged vital sign values may be used. In one embodiment, all vital signs used are sampled at the same rate, irrespective of what the rate is in the range of 15-second to 5-minute average value sampling. It is also contemplated that a different statistic such as the median value or a quartile value can be used instead of the average value of the vital signs in such sampling windows.

In all aspects, the vital signs are sampled by the sensors 105, 107, and 109 at a rate that relates in some way to the cardiopulmonary control system response rate of human physiology. In other words, in order to capture the relevant behavior of human physiology as relates to profiling cardiopulmonary health, the vital signs are sampled at a rate that reveals the way the human system responds to cardiopulmonary challenge or exertion challenge. This is typically measured in the range of seconds to low minutes.

In still other aspects and while a full day has been set forth as a preferred time window on which to base the cardio profile, other time windows may be used in the present approaches. For example, the time windows can be longer. It is unlikely an individual's health will change drastically in a two-day period versus a one-day period. Therefore, more than 1440 minutes (one day) of one-minute data can be used, and possibly widening the time window up to a (small) multiple of that figure. Widening the window too much begins to risk having data that spans an actual change in health, especially for chronically ill patients who may deteriorate markedly over several days. In one alternative, a two-day (2880-minute) window can be used to generate a cardio profile, by way of example. This window can be moved in increments overlapping by a day, or some other overlap, to provide outputs on a daily basis.

Windows shorter than a day risk not including all relevant physiological behavior, so that different time windows represent substantially different types of behavior. For example, if the time window is 8 hours, then a first time window may represent mostly sleep, while the next 8-hour period may represent exclusively awake activity. This may result in a high variance in the output from assessment to assessment. In view of all of this, an alternative approach selects the time windows to exclusively focus on one behavior mode, such as awake-only or asleep-only. Such windows may be selected by fixed time periods, or may be selected by a distinct analytical algorithm known in the art such as sleep detection using actigraphy.

In other examples, other vital sign ensembles may be used. Heart rate (or pulse rate) and activity are primary indicators of the behavior of human cardiopulmonary dynamics. Respiration rate is also important, but is a pseudo-voluntary vital sign which may introduce modeling noise, since an individual can choose to talk (interrupt normal breathing) even while climbing stairs, for example. HRV, tilt, arrhythmias like A-Fib, are useful contextual vital signs.

As mentioned, filtered versions of the vital signs can be used as distinct inputs (such as low-pass and high-pass HR). This can be done for RR, ACT or HRV, for example. This may be desirable in order to separate out different underlying aspects of the behavior (gross movement vs fidgeting, for example).

Measures of tidal volume of breathing, cardiac output, blood oxygenation (SpO2) and blood pressure are primary candidates for extending or modifying the vital sign ensemble used, since they reflect the same cardiopulmonary performance being captured. For example, the vital sign ensemble may be extended by wearing a patch and a watch worn in tandem to provide at least HR, HRV, Tilt, RR, Pulse, Activity and Continuous Blood Pressure. In another embodiment, a watch only can be worn to provide Pulse, HRV, Activity, RR and Continuous BP.

Returning now to other elements of FIG. 1, the electronic network 110 is any type of electronic communication network or combination of networks such as the internet, a cloud network, a wide area network, a local area network, a wireless network, or a cellular network. Other examples are possible. The central processing center 112 is any central location (e.g., an office, company headquarters, data center, hosted virtual private cloud, or central laboratory) to which data is collected and analyzed. In this example, data from the humans 105, 107, and 109 is used to train the model 118 (or selected portions of the model 118 as explained elsewhere herein). Once trained, data obtained from the monitored human 124 is applied to the model to produce a current estimate of functional capacity (e.g., VO2Max) and this is used to perform various actions.

It will be appreciated that as used herein the term "control circuit" refers broadly to any microcontroller, computer, or processor-based device with processor, memory, and programmable input/output peripherals, which is generally designed to govern the operation of other components and devices. It is further understood to include common accompanying accessory devices, including memory, transceivers for communication with other components and devices, etc. These architectural options are well known and understood in the art and require no further description here. The control circuit 114 may be configured (for example, by using corresponding programming stored in a memory as will be well understood by those skilled in the art) to carry out one or more of the steps, actions, and/or functions described herein.

The database 116 is any type of electronic memory device that stores information electronically.

The mathematical model 118 may be one or more mathematical models that are stored electronically. In examples, the mathematical model may include an encoding neural network, a function generator neural network to generate weights when supplied with the cardio profile vector as input, an estimation neural network, and a functional capacity estimator. These elements are described in greater detail elsewhere herein.

Equipment 120 may be any type of equipment that may be used in the treatment of the human 124. In examples, the equipment 120 may be a drone or an automated vehicle that sends supplies or transports to the human 124. For example, the drone may navigate through the physical environment to the home of the human 124 to deliver supplies.

The fourth sensor 122 (associated with test or monitored human 124) senses one or more vital signs of the monitored human 124. The fourth sensor 122 may take the form of sensors 105, 107, or 109, or it may be of some other form or configuration that delivers the same vital signs used in training.

The mobile electronic device 126 is any type of mobile electronic device such as a smartphone, cellular phone, laptop, or tablet. Other examples are possible. As explained elsewhere herein various messages, alerts, or other types of information may be rendered at the mobile electronic device 126.

The treatment personnel or equipment 128 are medical personal (e.g., doctors, nurses, etc.) and/or medical equipment (e.g., heart monitoring equipment, surgical equipment, IV equipment) used by the medical personnel to treat human patients.

The medical personnel or equipment 130 are humans or equipment that is used to aid humans. For example, medical personnel or equipment 130 may be emergency personnel and vehicles that are dispatched to aid the human 124. The display 132 is any type of display device that renders information in any visual form (e.g., graphs, numeric values, alphanumeric characters, or charts) to users. For example, the display device may be of the same type as mobile electronic device 126 or may be a personal computer that is not mobile.

In one example of the operation of the system of FIG. 1, the model 118 includes an encoding neural network, a function generator neural network, an estimation neural network, and a functional capacity estimator. The encoding neural network is configured to accept as input a time series of a selected plurality of cardiopulmonary variables obtained from the sensors 105, 107, and 109, and to generate a multi-element cardio profile vector. The function generator neural network of the model 118 is configured to generate weights when supplied with the cardio profile vector as input.

The estimation neural network of the model 118 is configured to accept as input a time series of a subset of the selected plurality of cardiopulmonary variables obtained from the sensors 105, 107, and 109. The subset omits at least one excluded variable (e.g., heart rate), and the estimation neural network is configured to generate an estimate of the at least one excluded variable. The estimation neural network is configured by the control circuit 114 using the weights output by the function generator network as weights of connections between nodes in the estimation neural network.

Iterative training in tandem and by a plurality of iterations is performed on the encoding neural network of the model 118 by the control circuit 114 to produce a trained encoding neural network (which is also stored in the database 116) and on the function generator neural network to produce a trained function generator neural network (which is also stored in the database 116). The training uses an error metric inclusive of the difference between the at least one excluded variable and the estimate of the at least one excluded variable generated by the estimation neural network.

For each of the iterations, a first duration of training data 150 comprises a substantially contiguous time series of the selected plurality of cardiopulmonary variables from one of the training human subjects 104, 106, and 108 is input to the encoding neural network of the model 118. For each of the iterations, a second duration of the training data 150, substantially nonoverlapping in time with the first duration, comprises a substantially contiguous time series of the selected plurality of cardiopulmonary variables from the training human subject, and provides input to the estimation neural network of the model 118. The estimation neural network provides the estimate of the at least one excluded variable, which is usable in the error metric for training the encoding neural network and function generator neural network.

The functional capacity estimator of the model 118 is configured to accept as input a cardio profile vector generated by the trained encoding neural network. The cardio profile vector may be augmented with a preselected set of physical attribute values of the monitored human subject 124, and the functional capacity estimator outputs an estimate of a metric of functional capacity.

The functional capacity estimator of the model 118 is trained using a plurality of matched examples to produce a trained functional capacity estimator. Each of the matched examples comprises a cardio profile vector augmented with the physical attribute values from a person if any are used in the embodiment, matched with a corresponding measured functional capacity metric of that person, to enable regression of an input of a physical attribute-augmented cardio profile vector to an estimate of the metric of functional capacity.

The trained encoding neural network and the trained functional capacity estimator are deployed to accept as input (via the control circuit 114) a duration of monitored data 152 from the monitored human subject 124 obtained from the sensor 122. The monitored data 152 comprises substantially contiguous time series of the selected plurality of cardiopulmonary variables. The trained encoding neural network of the model 118 generates a current cardio profile vector for the monitored human subject 124. The current cardio profile vector may be augmented with physical attributes of the monitored human subject 124, such as weight, gender, body mass index, body fat percent, height, age, and the like. The cardio profile vector may additionally be augmented with an estimate of VO2Max calculated from the afore mentioned physical attributes. Other physical attributes of the monitored human subject are also possible, such as measures of lung volume, skeletal muscle mass, etc. The trained functional capacity estimator generates from application of the physical attribute-augmented current cardio profile vector to the trained functional capacity estimator a current estimate of the metric of functional capacity (e.g., VO2Max).

Based upon the current estimate of functional capacity, one or more actions are performed. In one example, the current estimate in a time series with prior estimates are displayed to a clinician (e.g., on display 132 or mobile device 126) for review of possible health changes in the monitored human subject. In other examples, the current estimate is compared to prior estimates and a test is performed for a change. An alert 154 is triggered to a clinician to investigate the health of the monitored human if a change is detected. The alert 154 may be rendered on the mobile device 126 or display 132.

In still other examples, the current estimate is compared to prior estimates and a test is performed for a change whereupon a questionnaire 156 (electronic or paper) is sent to the monitored human subject 124. For example, the questionnaire 156 may be electronically displayed on the display 132 or device 126 when these elements are with the monitored human 124. In yet other examples, the current estimate is compared to prior estimates and a test is performed to detect a change whereupon an entry is made in the medical record of the monitored human subject indicating a change in health of the monitored human subject occurred. The record may be at the database 116 or at some other database or location.

In further examples, the current estimate is compared to estimates from other monitored human subjects, in order to quantify health affects between at least a control group receiving a first intervention and a test group receiving a second intervention in a clinical trial. This information can be displayed to users at the devices 126 and 132, or annotated in the database 116 or at some other database or location used for collecting clinical trial results. In still other examples, the operation of a medical device (e.g., equipment 120) is controlled or a parameter of the medical device is set by a control signal 162 sent by the control circuit 114 where the medical device is associated with treating or monitoring the monitored human subject. In another example, a dispatch signal 158 can be sent to medical personnel or equipment 130.

In another example of an action, a treatment plan 160 may be created and sent by the control circuit 114 to treatment personnel or equipment 128. The treatment plan 160 may result in medicine being dispensed or medical equipment being adjusted, directed, or controlled.

In other aspects, data augmentation may be applied to the data obtained from the training population 102. Data augmentation is the manipulation of an existing set of data available for training, to create a much larger set of examples for training. In the approaches described herein, this can be achieved by selecting numerous start times for the 24-hour period comprising Day 1; selecting numerous offsets from end of Day 1 until start of Day 2 (e.g., immediately, delay 2 hrs, delay 36 hours, delay 12 hours 34 minutes, etc.); reversing Day 1 and Day 2 data; and generating a day comprising N hours from one 24 hour period with 24-N hours (likely analogous time of day) from another 24 hour period (e.g., morning from Day Z, afternoon from Day Z+1). Other examples are possible.

As a result, an enormous quantity of Day 1/Day 2 combinations can be generated from a modest number of subjects for whom a week to many weeks of contiguous data are available. Likewise, the number of VO2Max samples (for training a VO2Max network as described elsewhere herein) can similarly be amplified; a large number of Day1/Day2 pairs can be created for each VO2Max value, from a modest set of individuals for whom VO2Max results are available. All of these manipulations faithfully maintain data authenticity (i.e., still represent true pairings and are related by physiology) while posing to the network(s) variations in data that allow the network(s) to generalize their feature extraction.

Data for each of the channels (vital signs) may be normalized. In aspects, this involves establishing z-score parameters for each input variable (e.g., HR or RR) based on the statistics of all samples across all individuals comprising the training data set. All inputs, thereafter, including in estimation mode, are then converted to z-scores as well, using these statistics. The z-score, or "standard score" of a given vital sign value is equal to the quantity of the vital sign value minus the mean of the vital sign across all samples, said quantity divided by the standard deviation of the vital sign across all samples.

Figure 2:
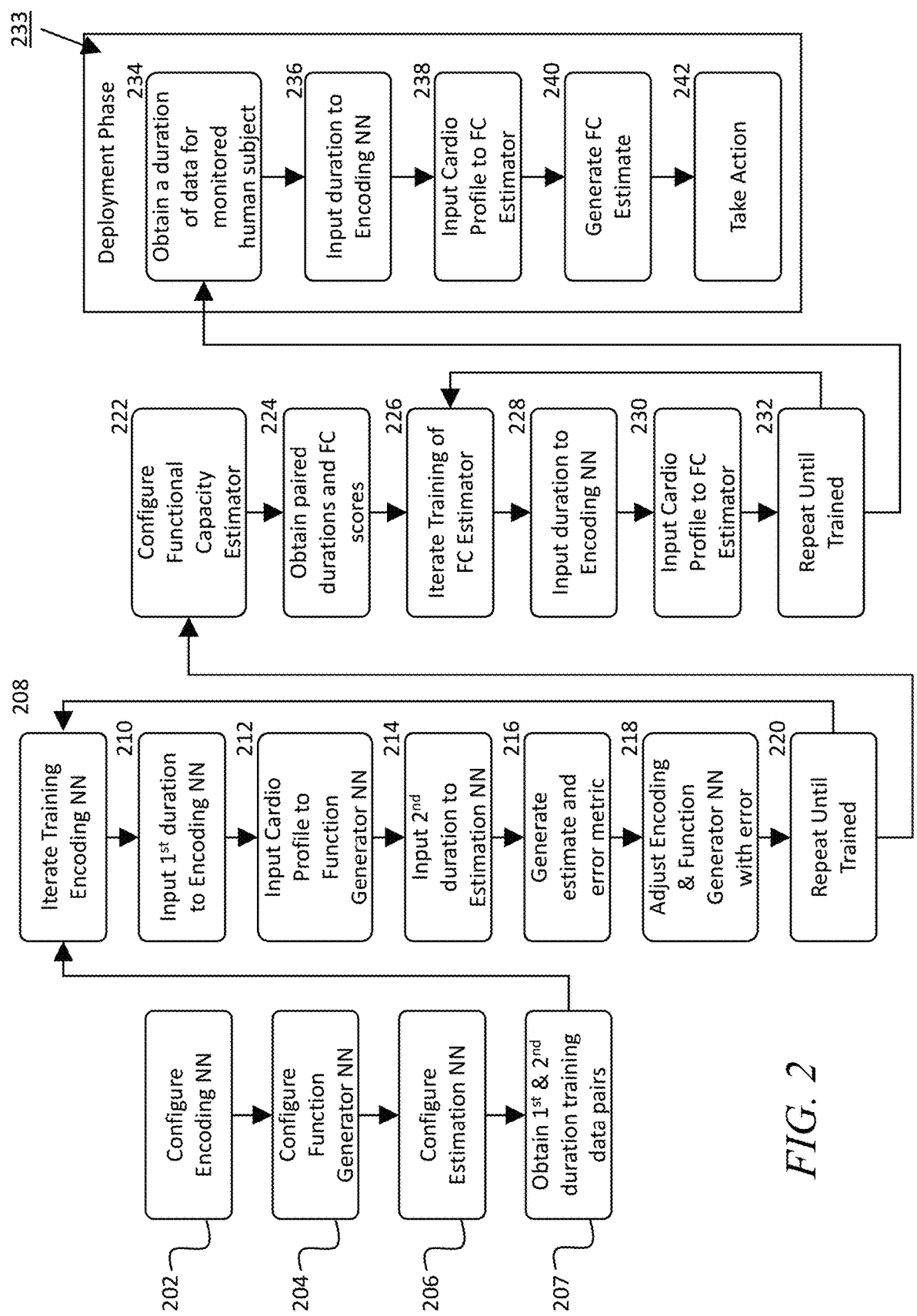
FIG. 2 comprises a flowchart as configured in accordance with various embodiments of these teachings.

Referring now to FIG. 2, one example of an approach for determining an estimate of VO2Max (or some other functional capacity metric) of a monitored human subject is described. The approach of FIG. 2 utilizes an encoding neural network, a function generator neural network, an estimation neural network, and a functional capacity estimator that together comprise a model.

At step 202, the encoding neural network is configured to accept as input a time series of a selected plurality of cardiopulmonary variables, and to generate a multi-element cardio profile vector.

At step 204, the function generator neural network is configured to generate weights when supplied with the cardio profile vector as input.

At step 206, the estimation neural network is configured to accept as input a time series of a subset of the selected plurality of cardiopulmonary variables. The subset omits at least one excluded variable. The estimation neural network generates an estimate of the at least one excluded variable, and the estimation neural network is configured using the weights output by the function generator network as weights of connections between nodes in the estimation neural network.

In step 207, first and second durations of multivariate time series vital signs data are obtained for use in training. Each pair of durations represents temporally close data representing in vital sign data the same physiological behavior of a training human subject, in general unconstrained and across typical activities of daily living.

At step 208, iterative training of the encoding neural network and the function generator neural network occurs. The iterative training occurs in tandem and is made by a plurality of iterations of the encoding neural network to produce a trained encoding neural network and of the function generator neural network to produce a trained function generator neural network. The training uses an error metric inclusive of the difference between the at least one excluded variable and the estimate of the at least one excluded variable generated by the estimation neural network.

For each of the iterations, a first duration of training data comprises a substantially contiguous time series of the selected plurality of cardiopulmonary variables from a training human subject is input to the encoding neural network. A second duration of the training data, substantially non-overlapping in time with the first duration but temporally close so as to represent the same physiological behavior, comprises a substantially contiguous time series of the selected plurality of cardiopulmonary variables from the training human subject, provides input to the estimation neural network and wherein the estimation neural network provides the estimate of the at least one excluded variable.

Within a given iteration, in a step 210 the first duration of times series data is input to the encoding neural network, which generates a cardio profile vector. In step 212, the cardio profile vector is input to the function generator neural network, and prospective network parameters such as weights are generated for use by the estimation network as its weights. Network parameters generated by the function generator network can be any network parameters that define a neural network, inclusive of weights and biases, but for purposes of this description shall be called weights comprehensively. In step 214, the second duration of time series data is input to the estimation neural network, which enables it to generate an estimate of the variable left out of the second duration input as described elsewhere herein. In step 216, an error metric is ascertained based on the differences between the estimated and held-out (but known) variable from the second duration of time series data. In step 218, this error metric is used to adjust the trainable weights and biases of the function generator neural network and the encoding neural network to move them toward producing outputs that enable the estimation network to produce a better estimate of the held-out variable. This iterative training is continued at step 220 until the networks in question are deemed sufficiently trained.

Then, at step 222, functional capacity estimator is configured to accept as input a cardio profile vector generated by the trained encoding neural network. At step 224, matched examples from multiple human subjects are obtained of (1) a duration of data (of approximately the same variables from the same sensor type and sample count as those of step 207) and (2) a measured functional capacity metric collected from the same person, using a reference "gold standard" measurement technique (such as a cardiopulmonary exercise test with a metabolic cart for a metric like VO2Max). At step 226, the functional capacity estimator uses the plurality of matched examples to produce a trained functional capacity estimator. For each pair, at step 228 the duration of time series data is input to the encoding neural network to generate a cardio profile. In step 230, the cardio profile is input to the functional capacity estimator in order to generate an estimate of functional capacity which can be compared to the measured value of the pair for error-driven training. If a neural network is used as the functional capacity estimator, this training can be iterated between steps 226 and 232 until deemed trained, i.e., where error is sufficiently low and network improvement has tapered off, as is known in the art. If the functional capacity estimator uses a different regression technique, the duration (and resulting cardio profiles) and "gold standard" reference measurements of functional capacity are fitted as is known in the art to define the parameters that comprise the functional capacity estimator.

The cardio profile vector of each of the matched examples may be augmented in some embodiments with physical attribute values from the person, such as weight, gender, body mass index, height, age, and the like. The augmented cardio profile vector then becomes the input to the functional capacity estimator.

At step 233, the trained encoding neural network and the trained functional capacity estimator are deployed to accept as at step 234 an input a duration of monitored data from a monitored human subject. This data comprises substantially contiguous time series of the selected plurality of cardiopulmonary variables. A current cardio profile vector is generated for the monitored human subject at step 236. The current cardio profile vector may be augmented with physical attributes of the monitored human subject. From application of the physical attribute-augmented current cardio profile vector to the trained functional capacity estimator in step 238 a current estimate of the metric of functional capacity is generated in step 240.

Based upon the current estimate of functional capacity, one or more actions are performed at step 242. In one example, the action is displaying the current estimate in a time series with prior estimates to a clinician for review of possible health changes in the monitored human subject. In another example, the action is comparing the current estimate to prior estimates and testing for a change whereupon an alert is triggered to a clinician to investigate the health of the monitored human. In yet another example, the action is comparing the current estimate to prior estimates and testing for a change whereupon a questionnaire is sent to the monitored human subject. In still another example, the action is comparing the current estimate to prior estimates and testing for a change whereupon an entry is made in the medical record of the monitored human subject indicating a change in health of the monitored human subject occurred. In yet another example, the action is comparing the current estimate to estimates from other monitored human subjects, in order to quantify health affects between at least a control group receiving a first intervention and a test group receiving a second intervention in a clinical trial. In a further example, the action is controlling the operation or setting a parameter of a medical device associated with treating or monitoring the monitored human subject.

Figure 3:
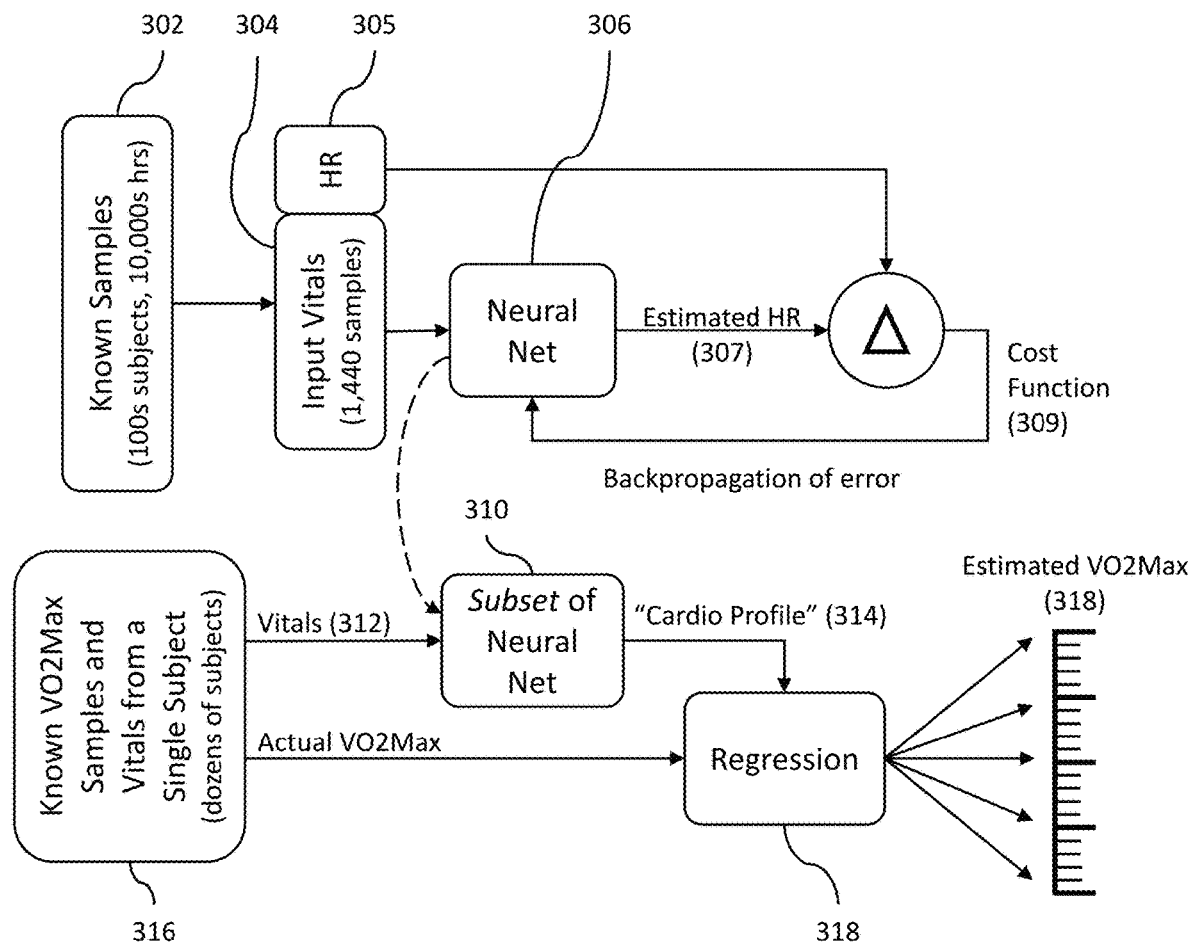
FIG. 3 comprises a diagram of a system as configured in accordance with various embodiments of these teachings.

Referring now to FIG. 3, a fundamental aspect is described of the approach to training the system of the invention for determining an estimate of VO2Max (or some other functional capacity estimate) of a monitored human subject based on vital signs reflecting activities of daily living. The approach takes advantage of training a neural network to accomplish a first task, namely inferential estimation of a held-out vital sign (like heart rate), to produce a trained network or subcomponent thereof that is well-adapted to provide an input to a second task, namely estimation of VO2Max or other functional capacity metric. FIG. 3 depicts the distinct two-step training process. Known input vital signs 304 (including an input vital sign heart rate (HR)) are obtained from samples 302. Samples 302 include a large group of samples from, for example, hundreds of different human subjects over tens of thousands of hours. The input vitals 304 are applied to a neural network 306 to produce an estimate value of HR 307. The estimate 307 is compared to the actual value 305 and the difference (cost function) 309 obtained. The cost function 309 represents an error that is back-propagated to the neural network 306 to train at least parts of the neural network. In this way, the neural network 306 is trained using tens or hundreds of thousands of samples from at least hundreds of human subjects.

Neural network 306 may be understood to comprise constituent neural architectures. Once trained, a subset 310 of the neural network 306 (e.g., the aforementioned encoding neural network) has vital signs 312 applied from a human subject for which known reference VO2Max measurement has been made. Application of the vital signs 312 to the subset 310 produces a cardio profile vector 314. Using dozens or hundreds of matched cardio profile vectors 314 and known VO2max samples 316, a regression to estimated VO2Max 318 can be trained or computed. Thus, once the above ensemble of networks is trained to generate the cardio profile vector, a much smaller set of VO2Max results can be used to perform a regression of the cardio profile to obtain estimated VO2Max 318. This can be done with any of a number of known regression techniques.

For instance, linear regression can be used. The cardio profile 314 is a vector of, say, 100 elements for each day of vitals data 312 from a human subject. The data can be fit to the corresponding measured VO2Max result for each human subject at 316, resulting in a linear model at 318 that maps the cardio profile vector of a human to an estimated VO2Max.

Decision trees, random forests, or a gradient boosting model can also be used. Decision trees can be configured to output a continuous-range parameter estimate (the VO2Max) for each cardio profile as an input. Random Forests and Gradient Boosting are extensions of basic decision tree methodology.

A Neural Network Estimator can be used at regression 318 as discussed below with respect to FIG. 5 and FIG. 6 and FIG. 15. In this case, error in estimating VO2Max compared to the known samples from 316 can be backpropagated to tune the weights of a neural network that takes the cardio profile 314 as input. A fully connected network could serve this role.

Figure 4:
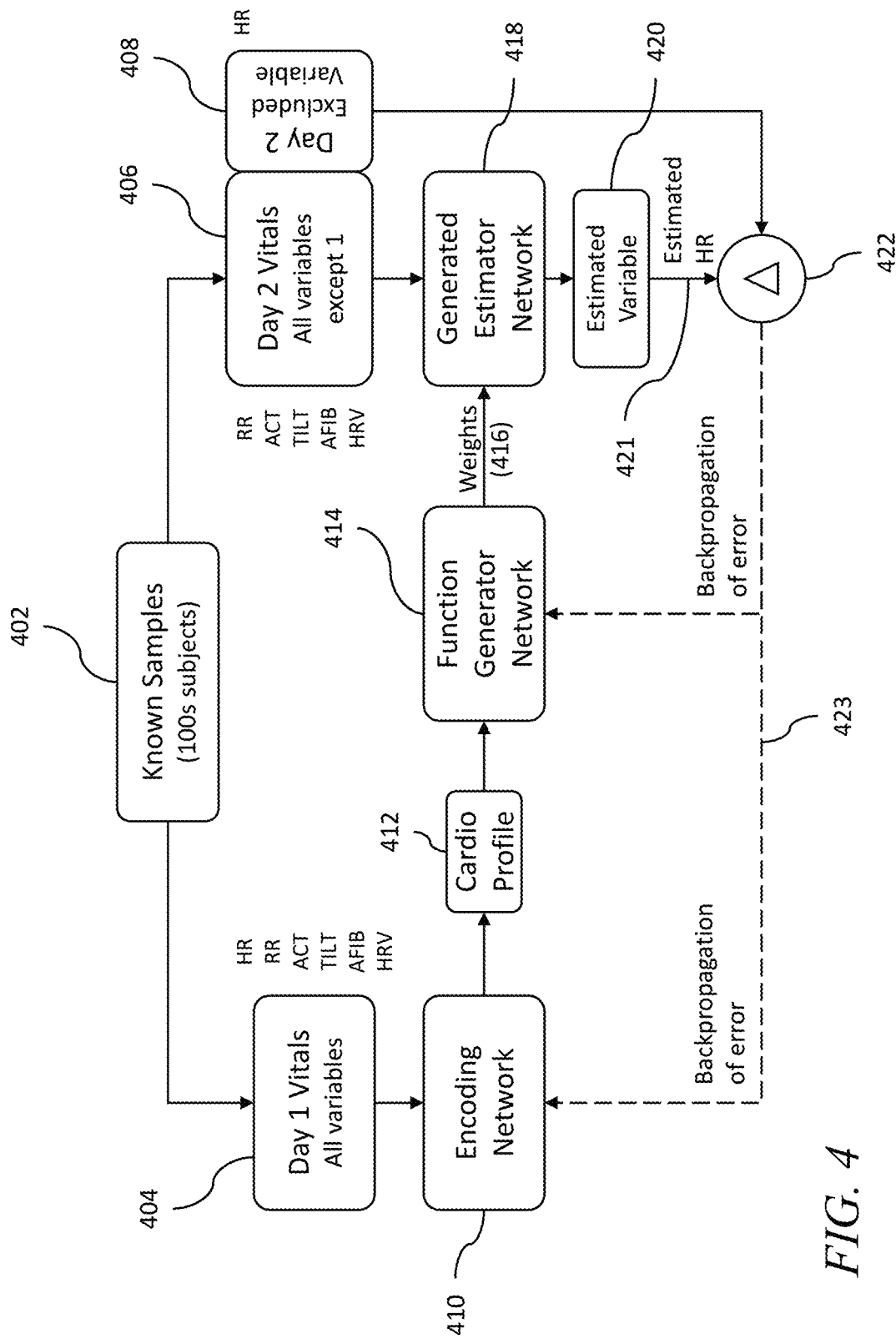
FIG. 4 comprises a diagram of a system as configured in accordance with various embodiments of these teachings.

Referring now to FIG. 4, one example of an approach for determining an estimate of VO2Max (or some other functional capacity value) of a monitored human subject is described. In aspects, this represents a more detailed version of the approach to training neural net 306 of FIG. 3.

Known samples 402 of days of vital signs from hundreds or more of human subjects include a first day ("Day 1") of vitals 404 for all variables (e.g., including heart rate, respiration rate, and so forth). Known samples also include a second day ("Day 2") of vitals comprising one variable 408 and a set 406 of all vitals except the one variable 408 (in this case the heart rate (HR)). It will be appreciated that Day 1 and Day 2 do not necessarily refer to information obtained on the same day, but across different (e.g., non-overlapping) time periods whether on the same calendar dates or different calendar dates. Day 1 data also does not necessarily occur in time before the Day 2 data. Day 1 and Day 2 data from the same subject should be used together; not Day 1 data from one subject, and Day 2 data from another subject.

The day 1 vitals 404 are applied to an encoding neural network 410. The encoding neural network 410 produces a cardio profile vector 412 that is applied to a function generator network 414. The function generator network 414 generates weights 416 that are used to set weight values in a generated estimation neural network 418.

Day 2 vitals 406 with all variables except one (in this case HR) are applied to the generated estimation network 418 to produce an estimate 420 of the held-out variable. The actual HR values are compared to the estimated HR 421 by difference function 422 to produce an error 423. The error 423 is backpropagated to the encoding neural network 410 and the function generator network 414 to further train these networks.

The encoding neural network 410, the function generator network 414, and the estimation neural network 418 are relatively deep neural networks, and in one specific example are Convolutional Neural Networks (CNNs). CNNs are optimized feature finders, and extract inherent features that matter against a backdrop of noise, for optimally effective categorization, or estimation of, for example, the held-out variable of Day 2. The feature extraction and mapping capabilities of the CNN utilize linear algebra effectuated by input values, intermediate non-linear or linear activation functions at "nodes" in the network and "weights" between those nodes to modulate the activation values. The final feature extraction and mapping capabilities of a trained neural net are tied up in the learned weights.

Throughout the day (or some other time period), a person engaging in ADLs exhibits dynamic changes in these vital signs due to exertion. Depending on cardiopulmonary health status, the individual's response spike may be higher/lower, delayed/not delayed; and the recovery from exertion may be normal/prolonged, by way of example. The absolute levels of exertion may differ between different individuals. These are the hints that need to be detected and mapped to an interpretable metric of cardiopulmonary health status. This data comprises vitals or samples 402.

The encoding neural network 410 is configured to learning the relationships between the vital signs from "Day 1" data and generating a "cardio profile" vector, characteristic of the cardiopulmonary dynamics of the individual ascertained from Day 1 data.

The function generator neural network 414 is configured to generate as its outputs the network parameters, such as weights and/or biases, of another neural network. It takes as input the cardio profile vector.

The generated estimation neural network 418 estimates HR for Day 2 data from an input of Day 2 data that does not include the HR. Its weights are dynamically generated by the function generator neural network 414 (based on the cardio profile it receives from the encoding neural network 410). The generated estimation neural network 418 does not "learn" its own weights independently. As such, the generated estimation neural network 418 produces an estimate of excluded variable (e.g., heart rate) 420 after input of Day 2 vitals 406. A difference operator 422 takes the difference between the actual value 408 of exclude variable and the estimate 420 to produce an error or cost function value 423.

Only the encoding neural network 410 and the function generator neural network 414 are trained using the cost function 423. The generated estimation neural network 418 is not trained; it gets the weights and biases of its node-node connections generated dynamically by the function generator neural network 414. However, it is the output of this estimation neural network 418 that creates the cost function value 423, namely the error between the estimated vital sign 420 and the actual measurements 408 of that vital sign. These errors 423 are not propagated back to the estimation neural network 418, but rather to the function generator neural network 414 and the encoding neural network 416.

In aspects, the training of the encoding neural network 410 and the function generator neural network 414 occurs as follows.

For training, iterate on:

(1) Day 1 data 404 is input to the encoding neural network 410. A cardio profile vector 412 is created.

(2) The cardio profile vector 412 is input to the function generator neural network 414, which generates the weights and/or biases of the estimation neural network 418.

(3) Input Day 2 data 406 (excluding the vital sign to be estimated) to the estimation neural network 418, which outputs estimated values 420 of the excluded vital sign.

(4) Determine error 423 as the difference between the estimated vital sign 420 and the known Day 2 vital sign 408.

(5) Backpropagate the error 423 into the function generator neural network 414 and the encoding neural network 410 to adjust their internal weights.

The training promotes the skill of the encoding neural network 410 and the function generator neural network 414 to create weights that make the estimation neural network 418 effective in outputting accurate vital sign estimates. Day 1 data is leveraged in the encoding neural network 410. In these regards, day 2 data is "unseen" by the encoding neural network 410 and function generator neural network 414, other than by the indirect process of error backpropagation. Hence, the encoding neural network 410 is effectively trained to generalize a feature set (the cardio profile) representing general cardiopulmonary function.

In aspects, the encoding neural network 410/function generator neural network 414 ensemble is trained using pairs of days from a population of individuals. The example individuals should span the range of health statuses expected to be seen in use. The day-pairs do not need to be in order or need to be adjacent calendar dates—but the day-pair needs to be from the same individual and need to be close enough in time to represent the individual at essentially the same health status. For example, it could be problematic to use a Day 1 from a heart failure patient that was 6 months earlier in time than a Day 2 from that patient, as the health of the patient could have changed somewhat in that 6-month time frame.

To summarize the above-described approach, training of the encoding neural network 410 and the function generator neural network 414 are accomplished using a cost function. Once the network architecture (e.g., number of layers, nodes in each layer, interconnectivity) is established, weights between connected nodes are randomly initialized. As described above, examples are input into the network, comparisons of the output of network to known labels or values associated with the input example are made, and a cost using the cost function (the error of the output compared to known true label/value) is determined, and the cost (error) is propagated backward in network, weights in the network at each layer are adjusted, and a test for convergence is performed. When sufficiently converged, the weights are frozen and in particular the trained encoding neural network (with the weights in its weight tables frozen) is deployed as part of an estimator of functional capacity, the regression training of which was described in connection with 318 in FIG. 3.

HR is included as an input to a cardio profile generating neural network 410, by training on a day 1 data, and then generalize this by using the learned relationships to estimate HR for day 2 data where the HR is not included as an input. In this way, the error on data not seen by the system is minimized. The cost function—the error between estimated HR and actual HR—is generated using data from an "unseen" day (day 2 data 406) to improve generalizability.

It will be appreciated that the generated estimation neural network 418 can be configured to make estimates of all the Day 2 vital sign inputs, and not just HR. (The penalty for inaccuracy is of course imposed on the upstream function generator neural network 414 and encoding neural network 410). This would be done on a round-robin basis, leaving out one vital sign and estimating it with the generated estimation neural network 418, then comparing the estimate of that excluded vital sign to the actual vital sign measurement. Since the generated estimation neural network 418 architecture is fixed, and the weights generated by the function generator neural network 441 need to work for each vital sign in a round-robin basis to error measurement, the architecture must accommodate all inputs and outputs, yet there is a need to hold-out each variable in turn to allow for inferential estimation. This is done by: (1) having a full input vital sign tensor (all minutes, all vitals) but masking out the vital sign to be excluded by setting its values to zero; and (2) having the network output estimates for all vital signs, but using only the vital sign that was masked out at the input in the cost calculation.

Figure 5A:
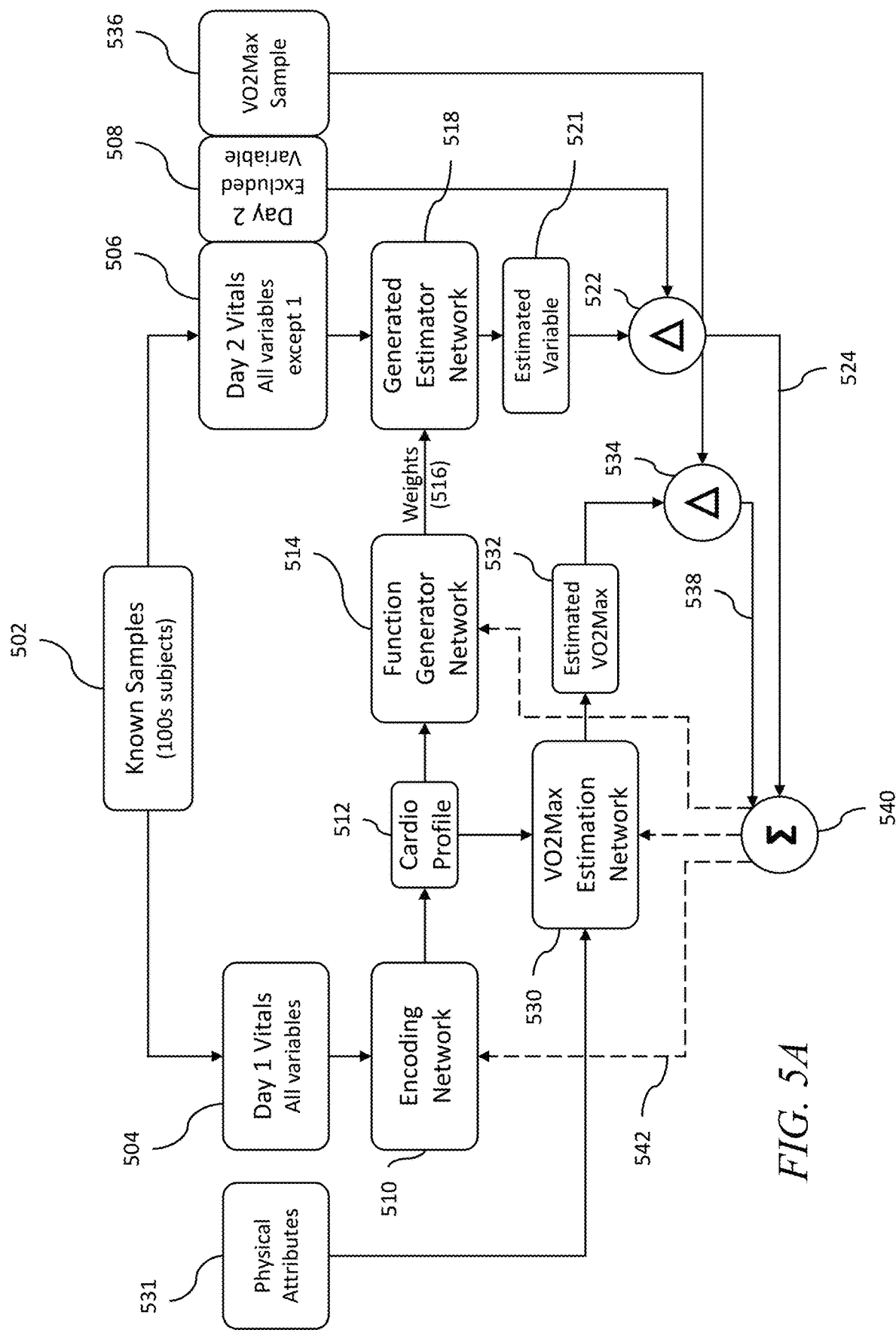
FIGS. 5A and 5B comprise diagrams of a system as configured in accordance with various embodiments of these teachings.

Turning to FIG. 5A, another example of training the neural networks of the invention is described. In this example, the training of an encoding neural network and function generator neural network are combined with training a neural network to serve as the functional capacity estimator for VO2Max estimation as shown. As explained below, the cost function is the combination of error from Day 2 vital sign estimation and VO2Max estimation. As before, a goal is to not require a large number (e.g., tens of thousands) of VO2Max results.

Many of the elements of FIG. 5A are the same as like-numbered elements of FIG. 4 and perform the same functions as described above with respect to the same elements in FIG. 4. These include known samples 502, which include Day 1 vitals 504 for all variables (e.g., including heart rate, respiration rate, and so forth). Known samples also includes Day 2 vitals 506 except one hold-out variable 508 (in this case the heart rate (HR); and in a round-robin approach, the hold-out variable for each round). It will be appreciated that Day 1 and Day 2 do not necessarily refer to information obtained on the same day, but across different (e.g., non-overlapping) time periods whether on the same calendar dates or different calendar dates, though close enough in time to represent substantially the same physiology of the person from whom they were acquired. The Day 1 data does not necessarily occur in time before the Day 2 day.

The Day 1 vitals 504 are applied to an encoding neural network 510. The encoding neural network produces a cardio profile vector 512 that is applied to a function generator network 514. The function generator network 514 generates weights 516 that are used to set weight values in generated estimation network 518.

Day 2 vitals 506 with all variables except one (in this case HR) are applied to the generated estimation network 518 to produce an estimate 521. The actual HR values are compared to the estimated HR values 521 by difference function 522 to produce an error 524 for Day 2 estimation.

The system of FIG. 5A includes a VO2Max estimation neural network 530. Cardio profile vector 512 is input to the VO2Max estimation neural network 530 along with physical attributes 531 of the individual to produce an estimated VO2Max 532, which is applied to difference operator 534. The difference operator 534 takes the difference between estimate 532 and an actual VO2Max sample 536 (measured with a "gold standard" reference method and associated temporally with the physiology of the human subject represented in the Day 1 and Day 2 data) to produce error output 538. Cumulative cost function operator 540 combines the output 538 and output 524 to produce a total error 542, which is applied to train the encoding neural network 510, the function generator neural network 514 and the VO2Max estimation neural network.

Training samples representing a large number of individuals will not have VO2Max results. A comparatively small number of samples will have VO2Max results. When VO2Max results are not available for a sample, the error for VO2Max will be set to zero, so that there is no driver of neural weight adjustment from that aspect of the system.

Once the encoding neural network 510, the function generator neural network 514 and the VO2Max Estimation neural Network 530 are fully trained, only the encoding neural network 510 and the VO2Max estimation neural network 530 need to be deployed for estimation of VO2Max on new subject data. Other regressors as mentioned above such as linear regression decision trees, etc., may take the place of the VO2Max Estimation Neural Network 530. This architecture is seen below with respect to FIG. 6.

Figure 5B:
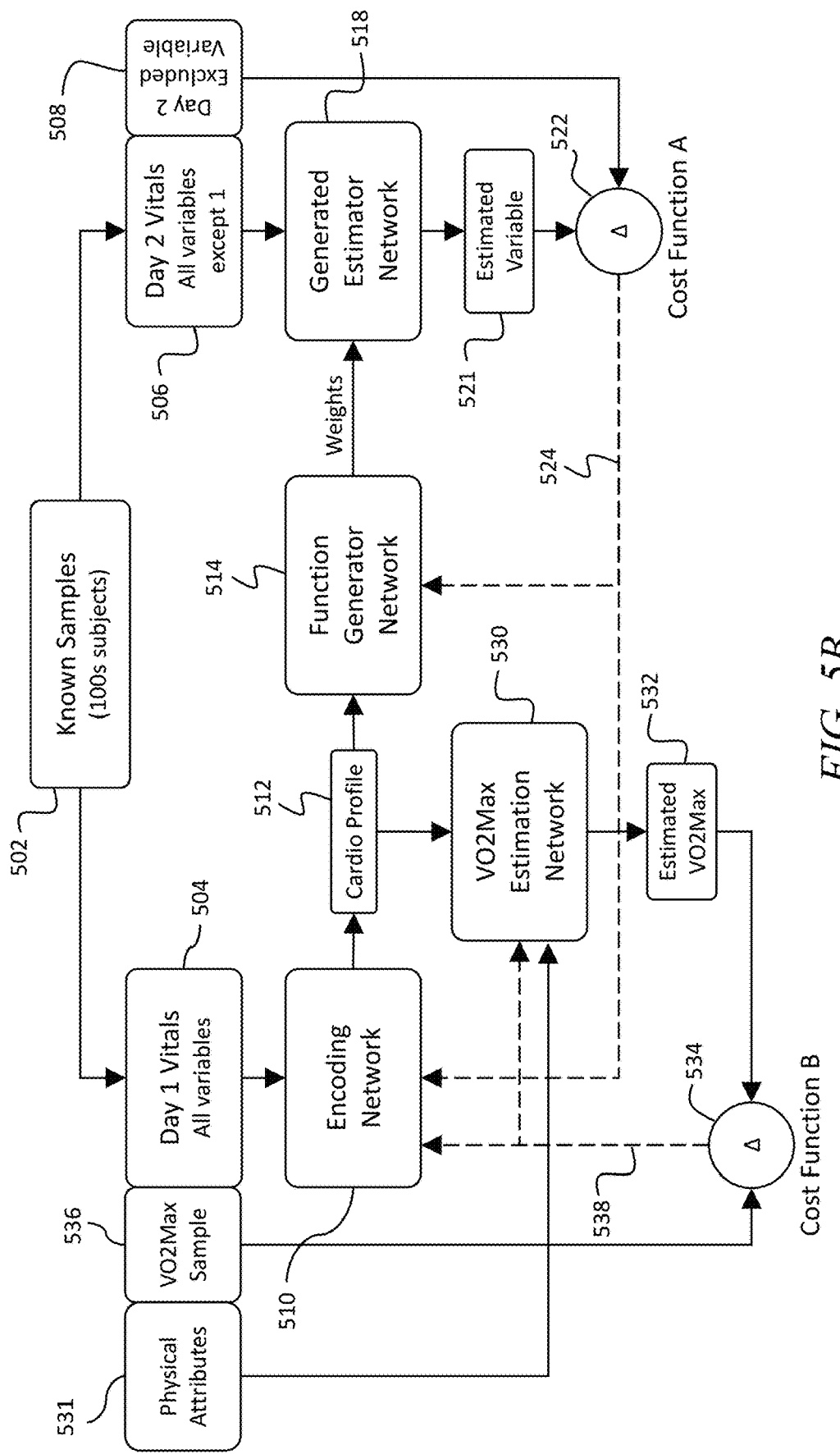

An alternative embodiment for training the encoding neural network 510 together with the VO2Max estimation neural network 530 is shown in FIG. 5B. The components of FIG. 5B are the same as in FIG. 5A with a few modifications. Whereas in FIG. 5A, the encoding neural network 510, the function generator neural network 514 and the VO2Max estimation neural network 530 are all trained together using the total error 542, in this FIG. 5B, this is separated into two phases of training. First, the encoding neural network 510 and the function generator neural network are trained together using the error 524 for Day 2 estimation that is output from difference function 522. Once this training is complete, in a second phase the encoding neural network 510 is trained together with VO2Max estimation neural network 530 (and without the involvement of the function generator neural network 514) using error output 538 produced by difference operator 534 when comparing estimated VO2Max 532 and actual VO2Max sample 536. Hence in this case, the encoding neural network 510 is trained to one state (part of a system that minimizes Day 2 estimation on held-out vital signs), and then from that state as a starting point, is further trained as part of a combination that minimizes error in estimating VO2Max.

Figure 6:
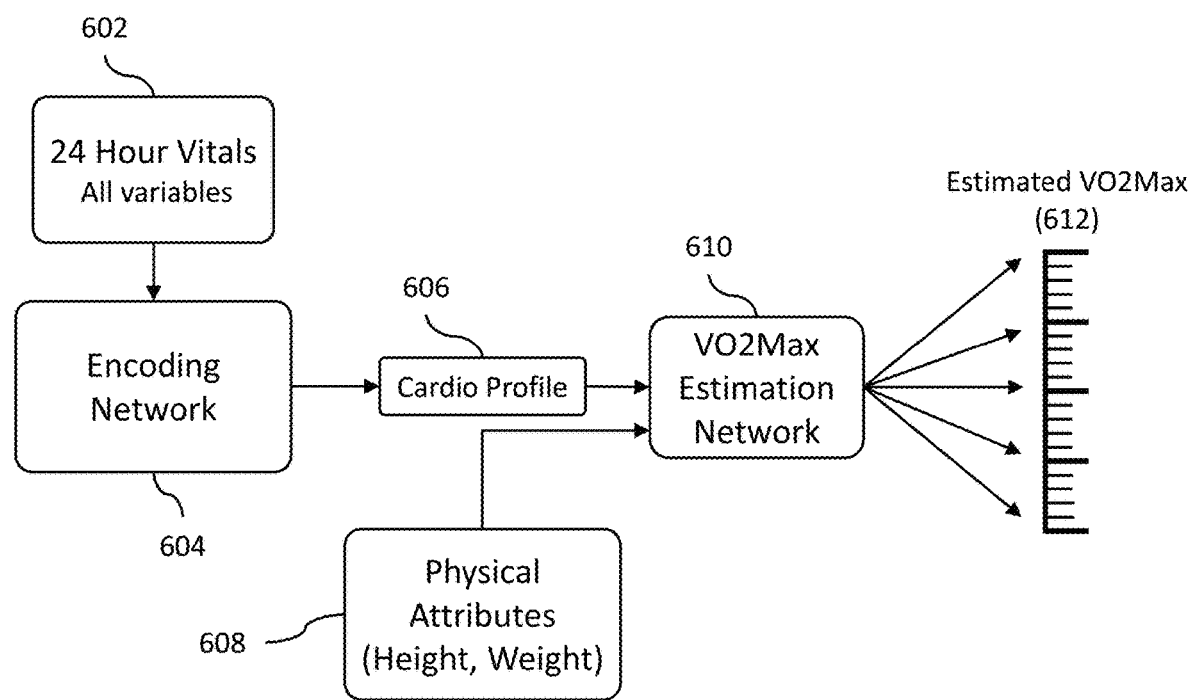
FIG. 6 comprises a diagram of a system as configured in accordance with various embodiments of these teachings.

Referring now to FIG. 6, one example of a system for estimating a functional capacity value, in this case VO2Max, is described. 24-hour vitals 602 (or vitals for some other period) of a monitored human subject are applied to a trained encoding neural network 604. The encoding neural network 604 has been trained, for example, as described with respect to the encoding neural networks described in FIGS. 4, 5A and 5B. Application of vitals 602 to the trained encoding neural network 604 produces a cardio profile vector 606.

Physical attribute values 608 may also be used by the VO2Max network 610. The VO2Max regression is performed with physical attribute values (height, weight, gender, age, body fat, etc.) in addition to the cardio profile as inputs to the VO2Max estimation regression. In some aspects, these additional inputs are critical to a VO2Max algorithms' success: an individual's VO2Max score is inclusive of their cardiopulmonary fitness as well as their physical attributes such as the size of their lungs. Information about their cardiopulmonary fitness is captured by the cardio profile, but the physical attributes of the subject must be additionally provided for an accurate VO2Max estimate.

The vector 606 is applied to a trained VO2Max network 610, which produces the estimated VO2Max 612. The VO2Max network 610 may be trained using a cost function as described with respect to FIG. 5A or 5B or in some other way.

Consequently and instead of measuring a large number (e.g., thousands), of VO2Max results which may be prohibitively time-consuming and/or expensive, a different value is estimated (e.g., heart rate) of which many examples can be obtained easily and in a cost-effective manner.

As mentioned, heart rate is one example of a variable to monitor. In some aspects, the neural networks of the present approaches are trained to estimate heart rate from the other vital signs, with the cost function being the mean squared error between the estimated heart rate and the actual heart rate. Large volumes of heart rate and the other vital signs data from many human subjects can be acquired easily and cheaply compared to capturing functional capacity metrics (like VO2Max) in clinical laboratory settings. With the approaches provided herein, there is no need to have the variable to be calculated (e.g., VO2Max) for all those subjects, since the neural network is now being trained to simply be good at estimating heart rate from the other data, not VO2Max. In doing so, the neural network combinations provided herein will effectively extract the same valuable features from the input data in order to do a good job at HR estimation, as it would in order to do a good job at VO2Max estimation.

While estimated HR may be a useful in itself from the neural network, it alone cannot be regressed against VO2Max samples in a useful way. What is obtained from the encoding neural network is an intermediate result that represents the "features" it has identified as important for estimating HR. These features are presumed to be equally important for estimating measures of cardiopulmonary performance, and hence VO2Max. The features can be found upstream of the HR estimation output of the generated estimation neural network, at a higher layer at the output of the encoding neural network, as the activations of the nodes in that layer. This layer of nodes provides a vector of activation values, which represent the presence or absence of the features that the neural net has learned to extract. This layer of activations (e.g., set at something between 40 and 100 nodes in the architecture) comprises a cardio profile vector of the individual from which the input data was taken. In other examples, the layer of activations includes around a thousand nodes. However, it will be appreciated that any number of nodes can be used. As is typical in a deep neural network, the features themselves do not necessarily lend themselves to direct interpretation—but comprise a vector of values that nonetheless represents key attributes of cardiopulmonary behavior in the ADL vital signs.

The cardio profile vector of, for example, 100 node activations at the critical intermediate layer, can then be conventionally regressed to estimate VO2Max, based on a regression using just dozens (50-200) of samples. This is far lower than the 10,000-1,000,000 samples that would be needed to train a neural net to estimate VO2Max directly. Moreover, the cardio profile can readily be regressed against other outputs, such as health categories or disease progression stages, instead of VO2Max.

Once the ensemble of above-described networks is trained to generate the cardio profile vector, these vectors can be regressed against categories of interest. A smaller set of category findings for individuals may be used with this invention than would be necessary if a typical neural network were directly trained on the categories. The regression against the categories of interest can be done by a number of techniques: Neural network classifier, Decision Trees/Random Forests/Gradient Boosting, Support Vector Machines, and K-Nearest Neighbor. Other examples are possible.

In deployed use and in one example, the system accepts a 24-hour input of vital signs, along with physical attribute values about the individual, and makes an estimate of the VO2Max represented by the dynamics of the vital signs in that period. The estimation mode utilizes both the population learning (training data from many people, with regression to "ground truth" VO2Max results), as well as a personalized cardio profile generated from the individual's ADL vital signs to map to the individual's instant estimated VO2Max.

Similarly, the cardio profile vector may be regressed against categories, such as the New York Heart Association (NYHA) Functional Classification; the Global Initiative for Chronic Obstructive Lung Disease (GOLD) criteria for classification of severity of airflow limitation in COPD; or other cardiopulmonary health category rating systems. It may also be regressed against other continuous variables customarily measured in clinical laboratory conditions, such as forced expiratory volume over 1 second (FEV1), lung functional residual capacity (FRC), lung residual volume (RV), maximal heart rate, VE/VCO2 slope, heart rate at the anaerobic and aerobic thresholds, cardiac output, stroke volume, ejection fraction, and predicted 6 minute walk test (6MWT) distance. The same principle of the invention applies in all cases: Since the encoding neural network is trained to generate a cardio profile vector encapsulating the essential features of learning the cardiopulmonary control system (the interplay of vital signs in ADLs) using a high volume of training samples across a population of subjects, the final regression or training of a second stage machine learning tool to map that profile to the desired categories or continuous variables can be performed with far less training data.

In one use case, the estimation of VO2Max successively day-over-day for an individual can be used to track the cardiopulmonary health status of the individual. This can be particularly useful for patients with chronic illness who are at risk to evolve over days or weeks from a stable state to an exacerbated disease state requiring hospitalization and acute care. By tracking the estimated VO2Max over time, a downturn may be detected which can be an early warning sign that the patient is deteriorating and may soon need acute care. Clinicians can intervene earlier to avoid the acute care episode.

In another use case, a clinical trial can be conducted to ascertain the effect of a drug, (implanted) device or other procedure or intervention on the health of subjects in the study. Estimated VO2Max can be used to replace conventional measures of health such as genuine VO2Max tests (too expensive to conduct multiple times on subjects in the study) or 6-minute walk tests (6MWT) (too coarse and inaccurate), and to provide more accurate and more frequent assessment of cardiopulmonary health status. This can be a state-of-the-art technique for evaluation of drug or device efficacy between control and test groups in a trial, and can provide more data samples per subject to improve extraction of the intervention effect, i.e., improve extracting the "signal from the noise".

In yet another use case, an insurance company interested to assure its insured members are receiving adequate preventative treatment for evolving disease conditions that are potentially expensive if not managed, can distribute to its members a sensor patch to wear for a week and upload data for analysis. In this case, the cardio profile may be regressed against categories of health previously determined from training samples. Once an insured member has worn the patch and uploaded data for analysis, the invention can match the individual to a category indicated by the cardio profile. This may identify members of the insured population who have a previously undiagnosed chronic disease, and facilitate getting the condition under management.

Figure 7:
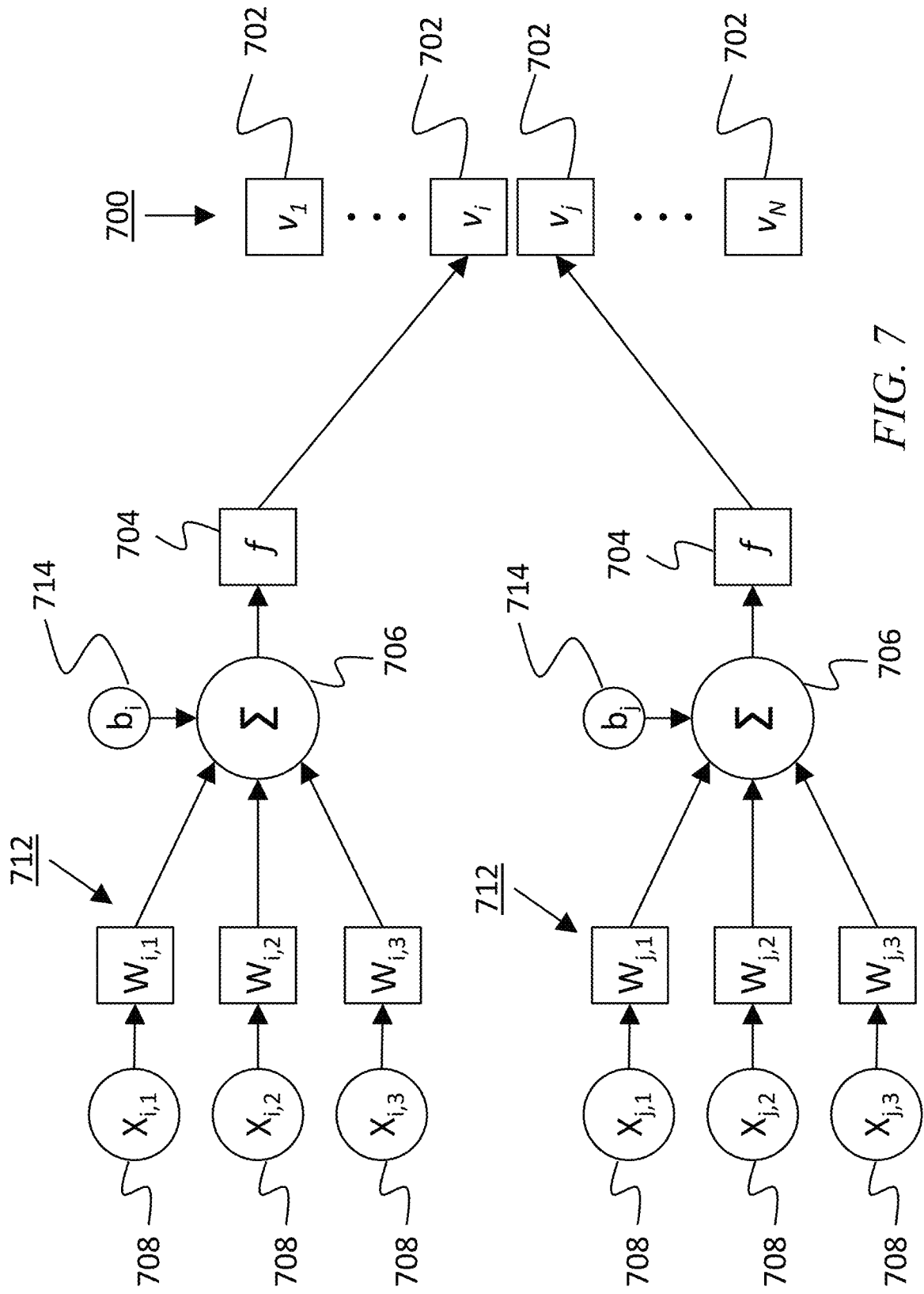
FIG. 7 comprises a diagram of a cardio profile vector and creating the vector as configured in accordance with various embodiments of these teachings.

Referring now to FIG. 7, one example of a cardio profile vector 700 is described. The vector 700 comprises a number of node output values 702, which have numeric values (e.g., real numbers or integers). These values are generated by means of an activation function 704 that represents the level of activation of the nodes 706 at the output layer of the encoding neural network. Activation functions may take the form of functions such as sigmoid, arctan, hyperbolic tangent, rectified linear unit (ReLU), leaky ReLU, exponential linear unit (ELU), and the like, which are known in the art. The vector may be generated by the encoding neural networks described herein. The number of such nodes (and thus the length of the vector 700) may be on the order of tens or hundreds of nodes, and in one embodiment hereof is 100 nodes. Each such node 706 receives inputs 708 from other nodes at higher or upstream layers of the network, which represent the activation values of those nodes. The inbound activation values are multiplied by learned weights 712 to yield numbers that are summed at each node 706. In this way, the inbound activation value from any given upstream node may be amplified or attenuated by the weight on that connection, as it contributes to the overall sum of inbound activations to the node 706. Added to that sum for each node 706 is a bias value 714 as well. Learned weights 712 and biases 714 are what get updated when the neural network is trained by backpropagation of error. Adjustment of these weights and biases improves performance of the neural network based on the task by which error is measured.

In aspects, the fields 702 represent an intermediate result of the features that an encoding neural network has identified as important for estimating a variable such as HR. These features are presumed to be equally important for estimating measures of cardiopulmonary performance, and hence VO2Max or other functional capacity variables or categories. As mentioned, the features can be found upstream of the HR estimation output of the neural network, at a higher layer, as the activations of the nodes in that layer. This layer of nodes will provide a vector of activation values, which will represent the presence or absence of the features that the neural net has learned to extract. The layer of activations (set at something between 40 and 100 nodes in the architecture) is the "cardio profile" vector 700 of the individual from which the input data was taken.

Figure 8:
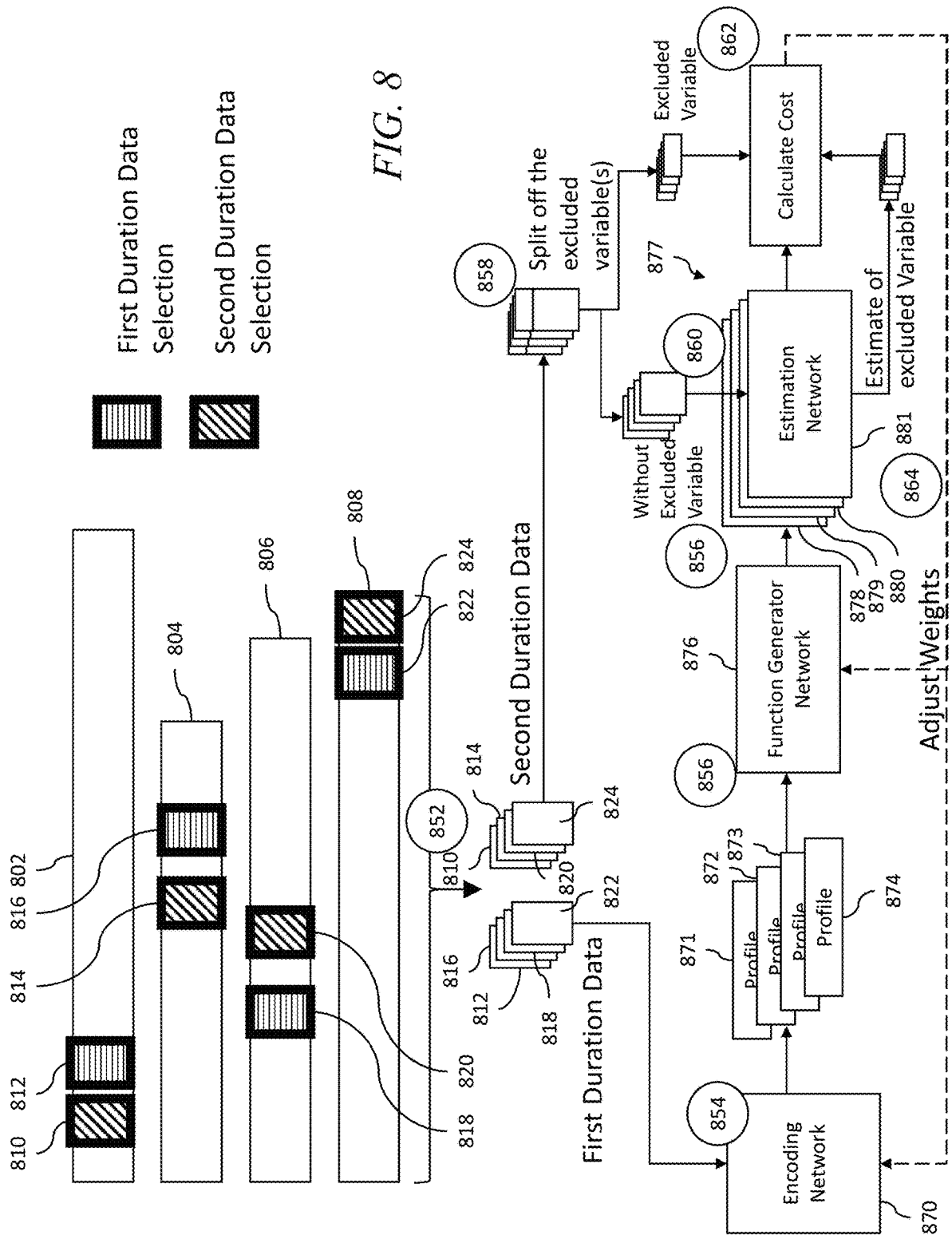
FIG. 8 comprises a diagram of a system as configured in accordance with various embodiments of these teachings.

Referring now to FIG. 8, an approach for training the neural networks used to estimate functional capacity (e.g., VO2Max) values is described. It will be appreciated that the approach presented in FIG. 8 represents one iteration of the overall training process and that the approach described in FIG. 8 is repeated multiple times (e.g., in one example, 100,000 times) to train the neural networks. In practice and in the first iteration, hundreds of pairs of duration data are selected from multiple subjects and the process of FIG. 8 performed. Then, in a second iteration hundreds of other data pairs are selected and the process of FIG. 8 performed again. After multiple (e.g., 100,000) iterations, the overall process is complete.

At step 852, data from four individuals of a training population is assembled. This data includes data from a first human 802, data from a second human 804, data from a third human 806, and data from a fourth human 808. Random pairs of duration data are selected from each data set 802, 804, 806, and 808. In particular, a first random pair (810, 812) of duration data is selected from the first human data 802; a second random pair (814, 816) of duration data is selected from the second human data 804; a third random pair (818, 820) of duration data is selected from the third human data 806; and a fourth random pair (822, 824) of duration data is selected from the first human data 808. As mentioned, other pairs likely exist, but only four pairs are shown for visualization purposes.

It will be understood that each of the pairs includes a first duration and a second duration. The first duration and the second duration do not have to be sequential in time; for some pairs, the first duration occurs before (in time) the second duration, and with other pairs the first duration occurs after (in time) the second duration. In the present example, first duration data includes data 812, 816, 818, and 822. Second duration data includes data 810, 814, 820, and 824.

At step 854, the first durations of data (812, 816, 818, and 822) are passed to an encoding neural network 870 (which is the same as the other encoding neural networks described herein). This responsively produces cardio profile vectors 871 (corresponding to the first human), 872 (corresponding to the second human), 873 (corresponding to the third human), and 874 (corresponding to the fourth human). As discussed elsewhere herein, the vectors may be vectors of real numbers representing cardio pulmonary characteristics of a human.

At step 856, the vectors 871, 872, 873, and 874 are applied to function generator network 876, which generates the weights that are used by estimation neural networks 877. The estimation networks 877 are actually a first estimation network 878 (having parameters tailored to vector 871), a second estimation network 879 (having parameters tailored to vector 872), a third estimation network 880 (having parameters tailored to vector 873), and a fourth estimation network 881 (having parameters tailored to vector 874).

At step 858, the second durations of data (810, 814, 820, and 824) are further processed so that at least one variable (e.g., heart rate) is excluded from that data. The data may be labeled (or recognized in some other way) and the data associated with the excluded variable is removed.

At step 860, the second durations of data (810, 814, 820, and 824), now having the excluded variable removed, are sent to the estimation neural networks 877, which, for each of the four individuals creates estimates of the excluded variable (e.g., heart rate). More specifically, data 810 (with excluded variable removed) is applied to the first estimation network 878 (having parameters tailored by vector 871), data 814 (with excluded variable removed) is applied to the second estimation network 879 (having parameters tailored by the vector 872), data 820 (with excluded variable removed) is applied to the third estimation network 880 (having parameters tailored by vector 873), and data 824 (with excluded variable removed) is applied a fourth estimation network 881 (having parameters tailored to vector 874).

At step 862, the cost (mean squared error between the excluded variable and the estimated excluded variable) is determined. This may be performed for each individual human and the overall error calculated as a sum.

At step 864, the error calculated at step 862 is back-propagated to the function generator neural network 876 and the encoding neural network 870. Propagation in these networks adjusts weights in these networks so that the cost (error) produced by these networks is reduced.

Figure 9:
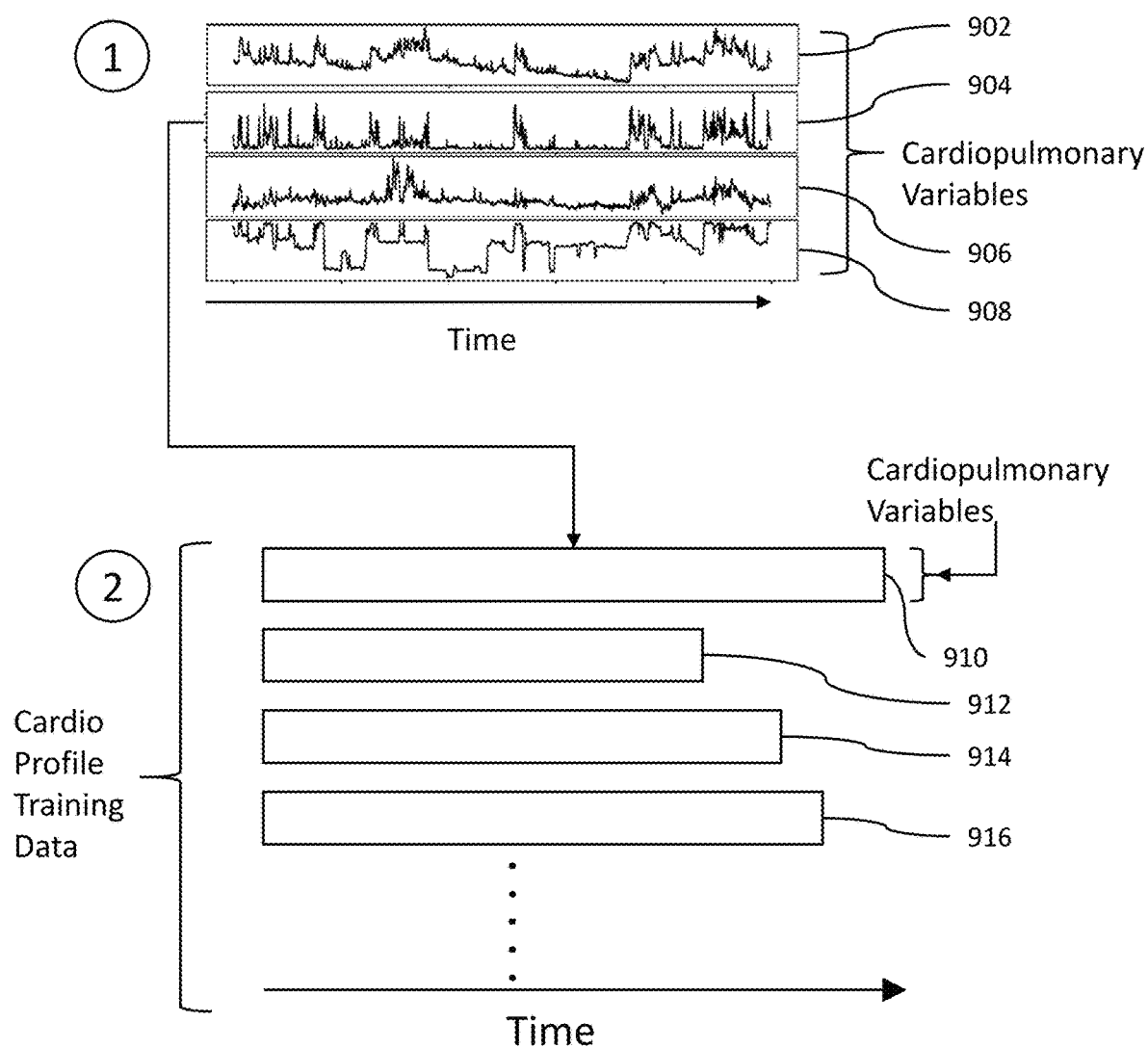
FIG. 9 comprises a diagram of a system as configured in accordance with various embodiments of these teachings.

Referring now to FIG. 9, one example of obtaining training data is described. Cardiopulmonary variables 902, 904, 906, and 908 are collected over time, and may represent vital sign values determined at a common sampling rate, such as once per minute, or once per 15 seconds, as two examples. Such cardiopulmonary variables are recorded together. The total number of vital signs may of course be more than just four. The recorded cardiopulmonary variables from individual humans 910, 912, 914, and 916 form the training data, with the total data contribution from each human varying on the order of days to weeks. With reference back to FIG. 8, the cardiopulmonary variables are collected as data sets for a first person 802, a second person 804, a third person 806, and a fourth person 808, of many subjects. The training data in total is composed of data from hundreds of individuals who have completed data for multiple weeks.

Figure 10:
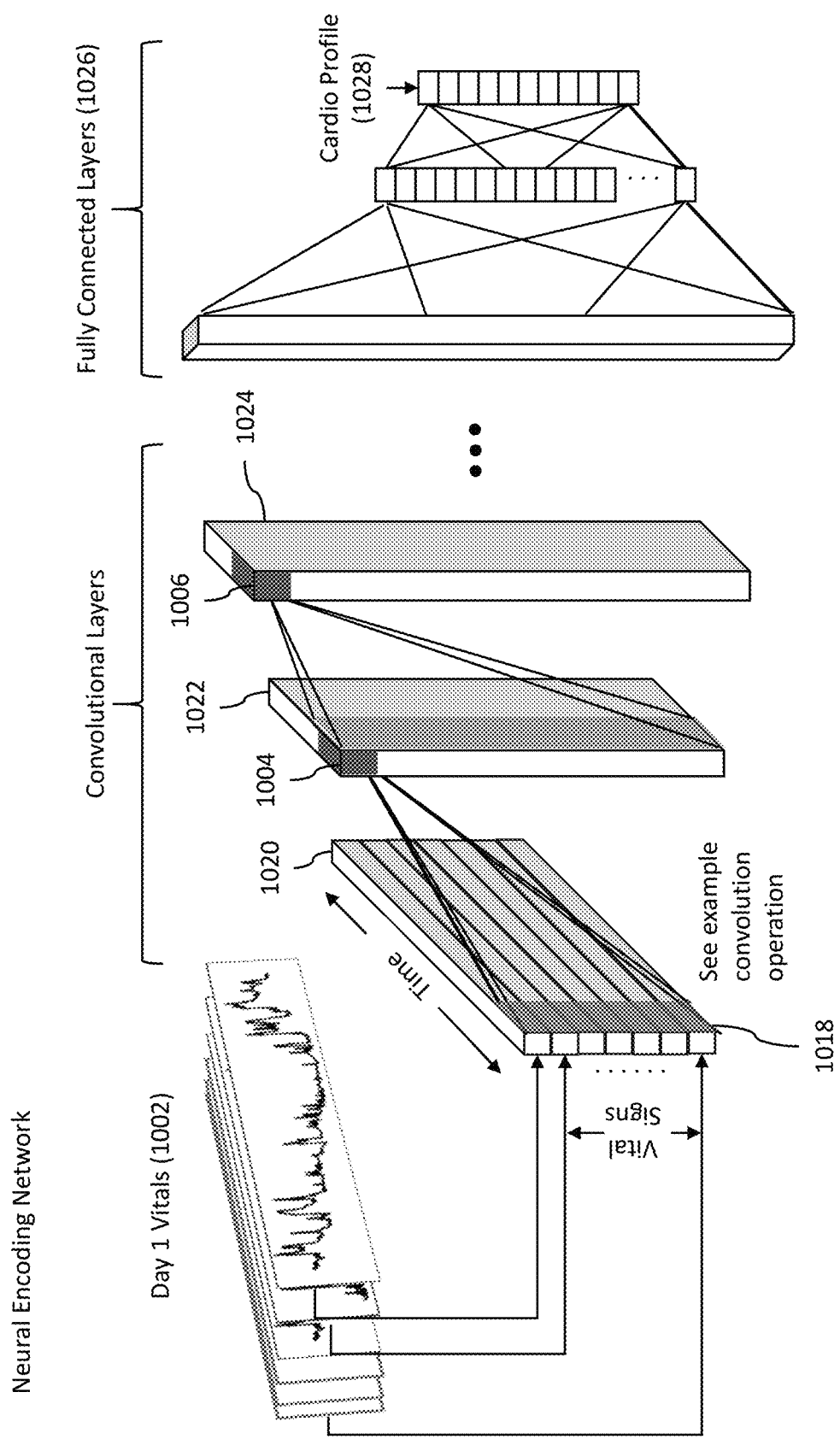
FIG. 10 comprises a diagram of a system as configured in accordance with various embodiments of these teachings.

Referring now to FIG. 10, one example of the architecture of the encoding neural network is described. Day 1 vitals 1002 (e.g., from the first duration as mentioned in FIG. 8) is applied to a first layer 1020 of an encoding neural network. The first layer comprises rows and column with each row representing the values of a particular vital sign over time, and where "columns" of data across the vital sign inputs are coincident in time. The input layer forms an 2D "image" of sorts, where the dimensions are (1) vital signs by (2) time. The architecture of this network is a convolutional neural architecture, and as such, a filter pattern comprising a set of node-to-node weights (as described for example in FIG. 7) is convolved with the input "image" by applying it to an area 1018 of the input and then sliding it to a next input area to apply it there, and so on, thereby convolving it with all input node activations. Area 1018 should encompass all variables (all rows) and can encompass a plurality of contiguous columns (e.g., a span of time). The set of weights comprising the filter pattern can differ from one another, but keep their values during convolution. It can be seen that convolution operations are performed on the first area 1018, where the set of weights are applied to the corresponding input layer values in the area 1018 and the weighted values summed to form an entry 1004 in a second layer 1022. Areas in this second layer are likewise convolved with a different filter pattern specific to that layer and summed to obtain an entry 1006 in a third layer 1024. This continues up to fully connected layers 1026. At fully connected layers, in contrast to the convolutional layers, all upstream nodes are fully connected to all downstream nodes and all have their own individual weights (as is known to those skilled in the art), so that a filter pattern of weights is not used at these layers. The cardio profile vector 1028 is an output of two or more fully connected layers.

Figure 11:
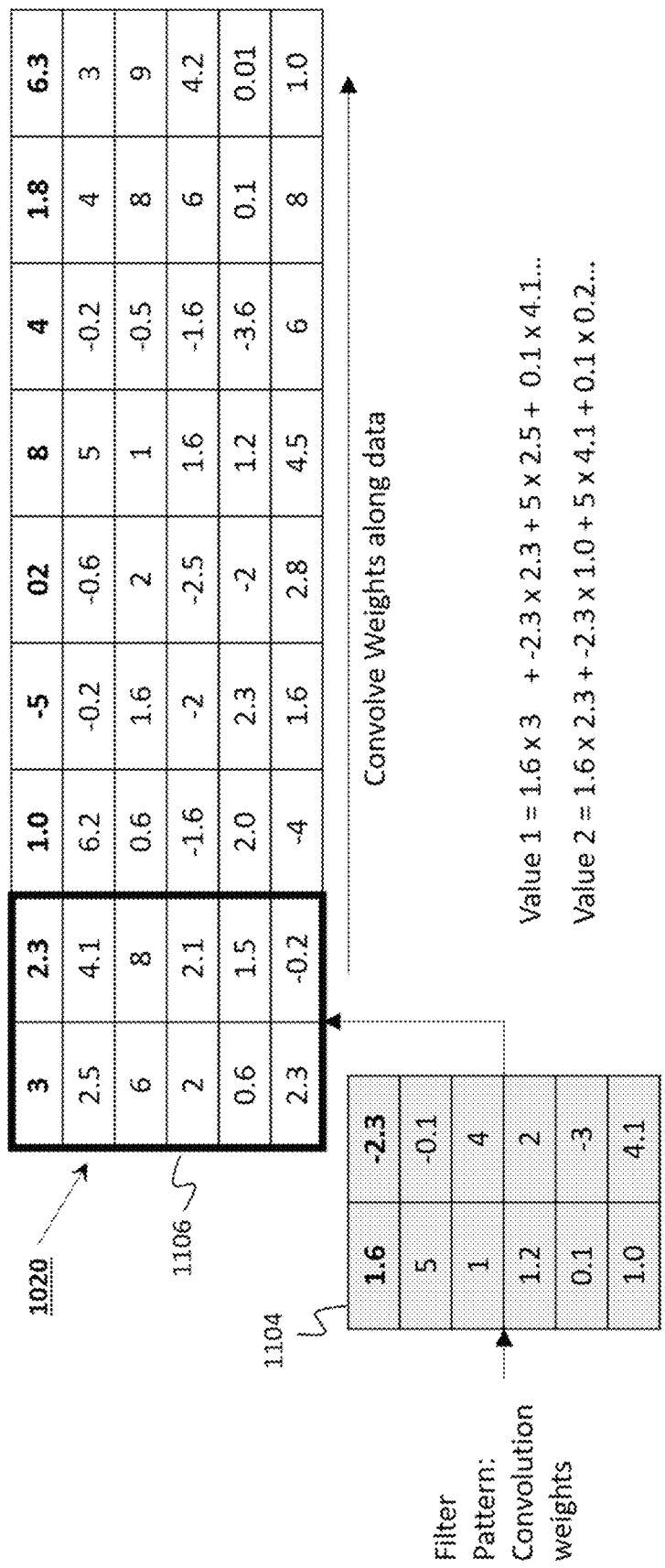
FIG. 11 comprises a diagram of a system as configured in accordance with various embodiments of these teachings.

Referring now to FIG. 11, a typical convolution operation as used in the encoding neural network is described in more detail. A layer like layer 1020 of FIG. 10 is represented as a series of rows and columns in a table of values that are the input data. A weight table 1104 comprises a filter pattern as described with respect to FIG. 10, and is applied to an area 1106 of the layer 1020. The weight table has as many rows (variables) as the layer 1020, but does not extend across all columns (all time samples) of layer 1020 and instead covers only some contiguous span of time. Values are obtained by multiplying a weight from the weight table with the corresponding value in the layer. The weighted values are then summed to provide the output value at the corresponding node of the next layer.

In this example, row 1, column 1 from the weight table is multiplied by row 1, column 1 of the layer 1020. Row 1, column 2 from the weight table is multiplied by row 1, column 2 of the layer 1020. Then, row 2, column 1 from the weight table is multiplied by row 2, column 1 of the layer 1020. This process continues as shown to produce a weighted sum (value 1 as shown in FIG. 11) where one weighted sum exists for the area filtered by the filter pattern.

The weighted table then slides to the right, for example, by one column (one time sample) and the process repeats to get value 2 as shown in FIG. 11. This is the process of convolving the filter pattern (weight table) across the input "image" to produce an output value for each step. This process is identical for deeper convolutional layers as well, not merely for the input layer (the input "image"). Note that the weights are the filter pattern as tabulated do not change as the filter pattern is convolved across the payer. In aspects, for each training iteration the weights are static. The weights in the filter pattern weight table are updated (by the error function back propagated as described herein) to reduce the error. Once the training is finished, the weights do not change.

Figure 12:
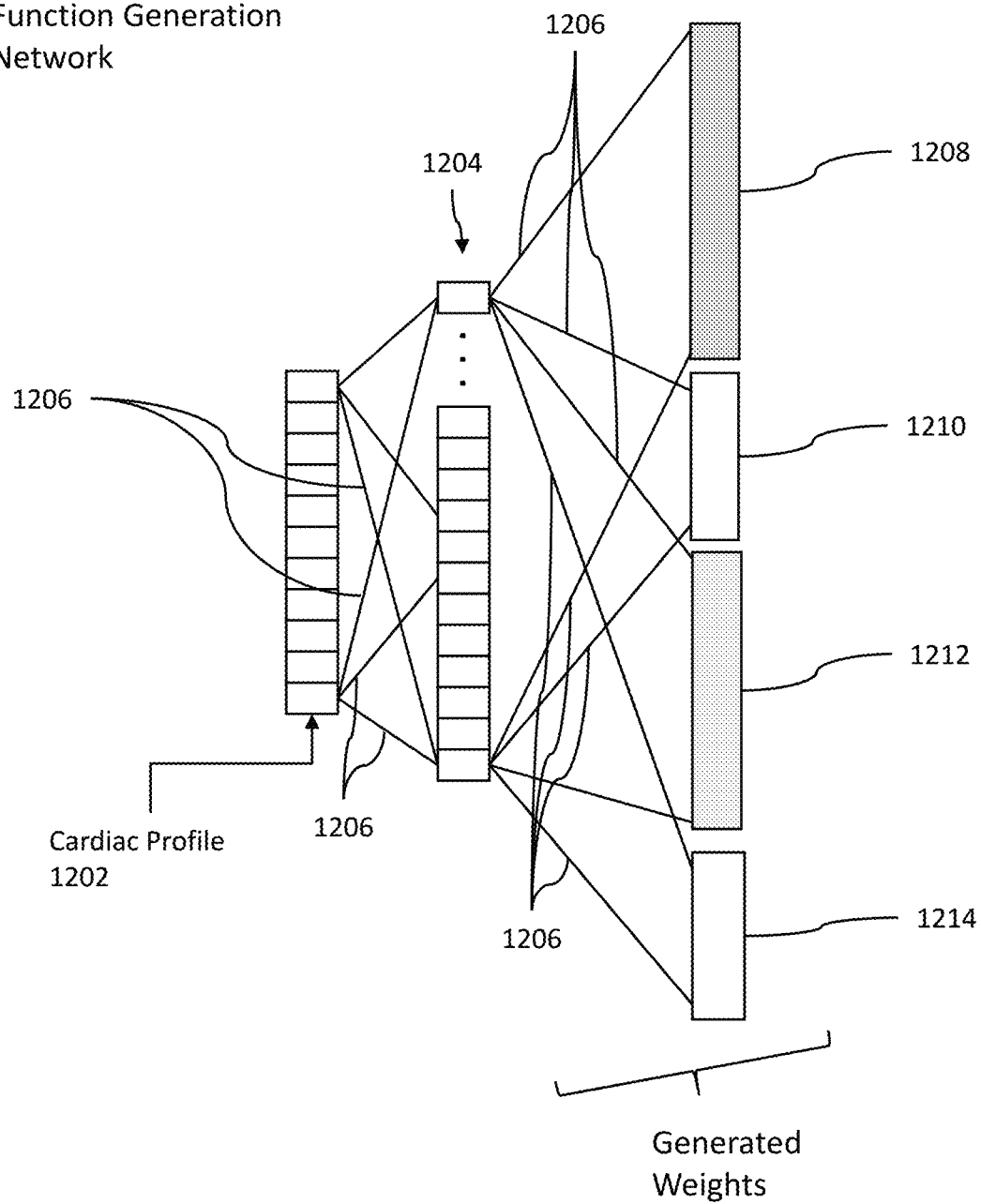
FIG. 12 comprises a diagram of a system as configured in accordance with various embodiments of these teachings.

Referring now to FIG. 12, one example of a function generator neural network is described. A cardio profile vector 1202 is the fully connected input layer to a first layer 1204 of the network. Connections 1206 are shown to generate outputs 1208, 1210, 1212, and 1214, the values of which will be used as weights and biases for the estimation network (the "Generated Weights") The function generator network is fully connected at each layer; that is, the weights connecting each upstream node to each downstream node are independent, unlike in a convolutional layer.

Figure 13:
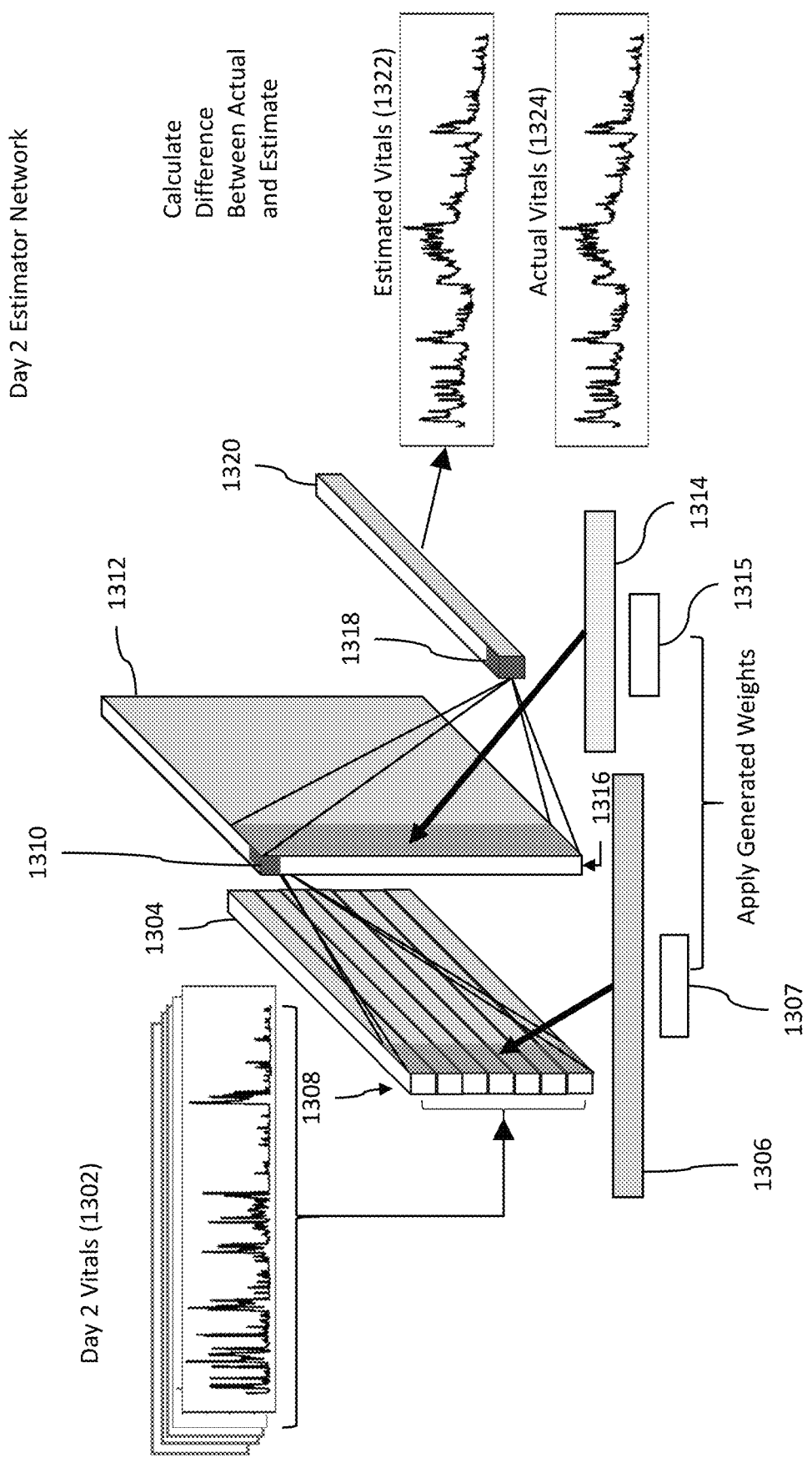
FIG. 13 comprises a diagram of a system as configured in accordance with various embodiments of these teachings.

Referring now to FIG. 13, the application of second duration data to the estimation neural network is shown. Second duration data 1302 (vitals from a person that excludes one variable such as heart rate) is applied to a first layer 1304 of the estimation neural network. As described before with respect to FIG. 10, layer 1304 comprises an "image" with variables making up the rows and time across columns. The estimation neural network likewise comprises convolutional layers. Weights (from the process of FIG. 12) are applied to filter pattern weight tables. Weights from weight table 1306 (provided as output weights 1208 from FIG. 12) and corresponding biases 1307 (provided as output biases 1210 from FIG. 12) are applied in a convolution process as has been described above with an area 1308 to produce entry 1310 in second layer 1312. Similarly, weights from weight table 1314 (provided as output weights 1212 from FIG. 12) and corresponding biases 1315 (provided as output biases 1214 from FIG. 12) are applied as has been described above with an area 1316 to produce entry 1318 in third layer 1320. Layer 1320 is the estimate 1322 of the values throughput the second duration of the excluded vital parameter (e.g., the heart rate). The estimated values 1322 are compared to the actual values 1324 of the heart rate to produce an aggregate error (mean, sum, or other statistical measure), which is used in back-propagation of error to the encoding neural network and the function generator neural network as described elsewhere herein. The error adjusts weights (e.g., in weight tables for filter patterns used in convolutional layers, or in node-to-node connections for fully connected layers) for these networks.

Figure 14:
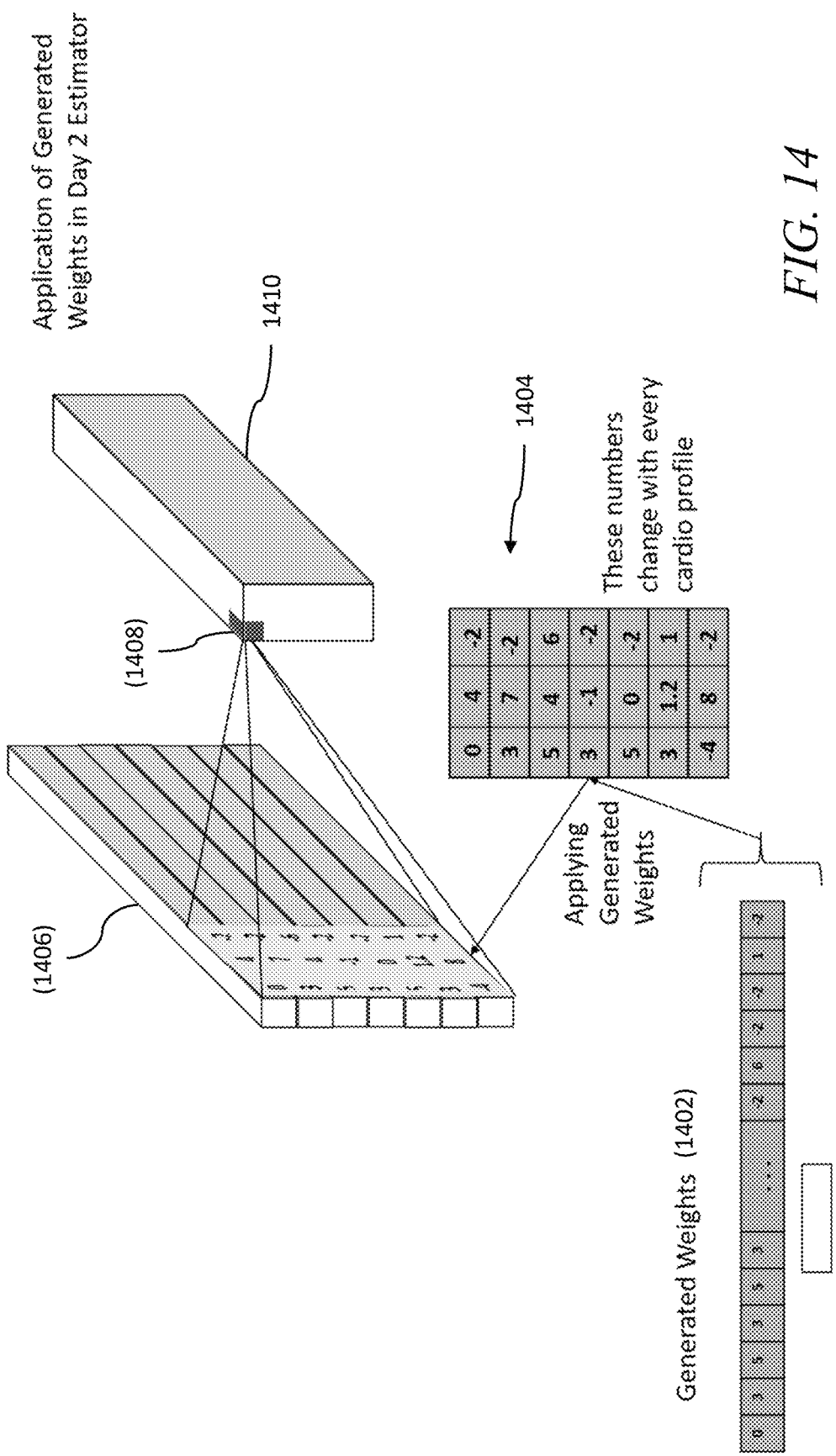
FIG. 14 comprises a diagram of a system as configured in accordance with various embodiments of these teachings.

Referring now to FIG. 14, one example of the application of generated weights 1402 (from the function generator neural network) to weight tables in estimation neural networks is described. The generated weights 1402 may be a vector of values, which fill in a weight table 1404. The first value is applied to row 1, column 1, the second value is applied to row 2, column 1, the third value is applied to row 3, column 1, and so forth.

The weights are applied in a convolution approach (described above with respect to FIG. 10 and FIG. 11) this time to a layer 1406 of the estimation neural network. These are convolved as has been described to form an entry 1408 in a second layer 1410. This continues to produce an estimate of an excluded variable when second duration data (modified to exclude the variable) is input to the estimation neural network.

Figure 15:
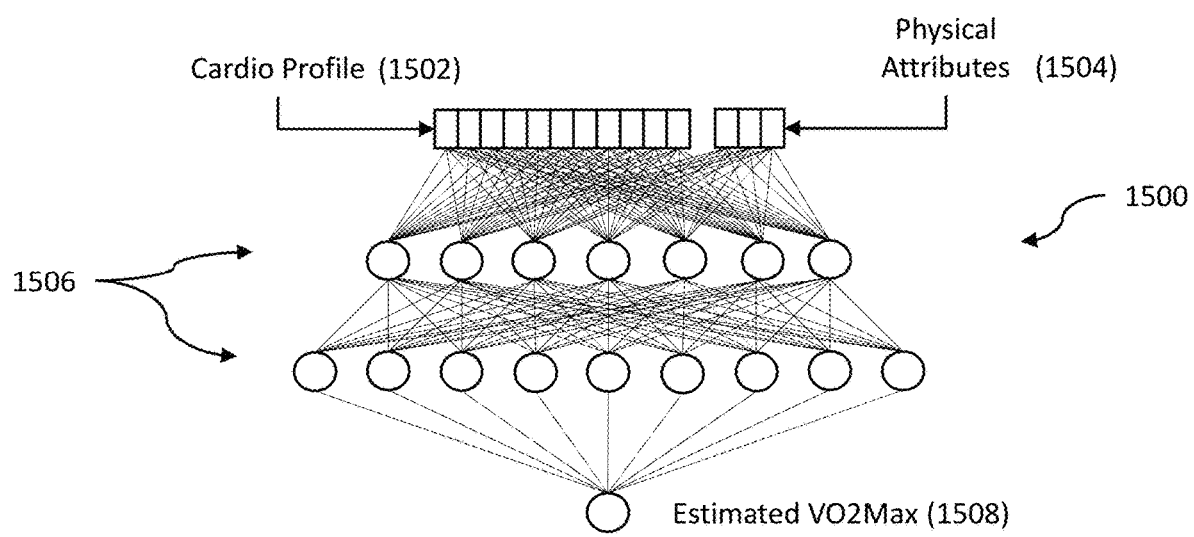
FIG. 15 comprises a diagram of a system as configured in accordance with various embodiments of these teachings.

Referring now to FIG. 15, one example of a VO2Max estimation network 1500 is described. As shown in FIG. 15, a cardio profile 1502 is input into the VO2Max estimation network 1500 along with augmenting physical attribute values 1504. The VO2Max estimation network 1500 consists of several fully connected layers 1506, culminating in an estimated VO2Max value 1508.

It will be appreciated that other neural network architectures often used for image and sequence analysis in the art may also be used instead of or in combination with the convolutional neural networks described in the encoding neural network and the estimation neural network. In other embodiments, one or both of the encoding neural network and estimation neural network may take the form of a causality preserving network such as a recurrent neural network, a temporal convolutional network, or a transformer (attention) network, among others.

Preferred embodiments of this disclosure are described herein, including the best mode known to the inventor(s). It should be understood that the illustrated embodiments are exemplary only and should not be taken as limiting the scope of the appended claims.

What is claimed is:

1. A method for treating and improving the cardiopulmonary health of humans, the method comprising:
deploying a trained functional capacity estimator, the trained functional capacity estimator having been produced by an application of a plurality of matched examples to a function capacity estimator;
receiving at the trained functional capacity estimator from a trained encoding neural network a current cardio profile vector for a monitored human subject, the current cardio profile vector having been generated by an application of a duration of monitored data from a monitored human subject to the trained encoding neural network, the duration of monitored data comprising a substantially contiguous time series of a selected plurality of cardiopulmonary variables;

generating from an application of the current cardio profile vector to the trained functional capacity estimator a current estimate of a metric of functional capacity for the monitored human subject;

wherein a selection has been made of a time series of a subset of the selected plurality of cardiopulmonary variables, the subset omitting at least one excluded variable, the time series of the subset of the selected plurality of cardiopulmonary variables being utilized by an estimation neural network to produce an estimate of the at least one excluded variable, and wherein the trained encoding neural network has been trained using an error metric inclusive of the difference between the at least one excluded variable and an estimate of the at least one excluded variable; and based upon the current estimate of functional capacity, performing one or more actions selected from the group consisting of:

displaying the current estimate in a time series with prior estimates to a clinician for review of possible health changes in the monitored human subject;

comparing the current estimate to prior estimates and testing for a change whereupon an alert is triggered to a clinician to investigate the health of the monitored human;

comparing the current estimate to prior estimates and testing for a change whereupon a questionnaire is sent to the monitored human subject;

comparing the current estimate to prior estimates and testing for a change whereupon an entry is made in the medical record of the monitored human subject indicating a change in health of the monitored human subject occurred;

comparing the current estimate to estimates from other monitored human subjects, in order to quantify health affects between at least a control group receiving a first intervention and a test group receiving a second intervention in a clinical trial; and controlling the operation or setting a parameter of a medical device associated with treating or monitoring the monitored human subject.

2. The method of claim 1, wherein the trained encoding neural network is trained by application of training data to an encoding neural network, and the trained encoding neural network is produced in a plurality of iterations, and for each of the iterations and for each of a plurality of training human subjects, a first duration of training data comprising a substantially contiguous time series of the selected plurality of cardiopulmonary variables from a training human subject is input to the encoding neural network, a second duration of the training data, substantially non-overlapping in time with the first duration, comprising a substantially contiguous time series of the selected plurality of cardiopulmonary variables from the training human subject, provides input to an estimation neural network and wherein the estimation neural network provides the estimate of the at least one excluded variable.

3. The method of claim 1, wherein the functional capacity is VO2Max.

4. The method of claim 1, wherein the time series of selected plurality of cardiopulmonary variables is obtained by sensors that are non-invasively secured to the skin of the humans.

5. The method of claim 1, wherein the time series of selected plurality of cardiopulmonary variables is obtained by sensors and the sensors are selected from the group consisting of: a camera, an electrocardiographic sensor, a light sensor, an accelerometer, an RF energy sensor, a temperature sensor, and a gyroscopic sensor.

6. The method of claim 1, wherein the functional capacity estimator generates the current estimate of the metric of functional capacity using one of: a linear regression technique, a decision tree, a random forest estimation, or a gradient boosting model.

7. The method of claim 1, wherein functional capacity estimator comprises an estimation neural network.

8. The method of claim 1, wherein the cardiopulmonary variables comprise one or more of: a heart rate, a measure of physical activity or motion, a time domain heart rate variability, a respiration rate, a tilt angle, an A-fib probability, and a sample time difference.

9. The method of claim 1, wherein the current cardio profile vector comprises a plurality of real numbers, each of the real numbers associated with one or more of the cardiopulmonary variables.

10. A system that is configured to treat and improve the cardiopulmonary health of humans, the system comprising:

a sensor for obtaining a duration of monitored data from a monitored human subject, comprising substantially contiguous time series of a selected plurality of cardiopulmonary variables, the sensor being deployed with a monitored human subject;

a control circuit, the control circuit coupled to the sensor, the control circuit being configured to:

receive from a trained encoding neural network a current cardio profile vector for a monitored human subject, the current cardio profile vector having been generated by an application of a duration of monitored data from a monitored human subject to the trained encoding neural network, the duration of monitored data comprising a substantially contiguous time series of the selected plurality of cardiopulmonary variables;

apply the current cardio profile vector to a trained functional capacity estimator;

generate from an application of the current cardio profile vector to the trained functional capacity estimator a current estimate of the metric of functional capacity for the monitored human subject;

wherein a selection has been made of a time series of a subset of the selected plurality of cardiopulmonary variables, the subset omitting at least one excluded variable, the time series of the subset of the selected plurality of cardiopulmonary variables being utilized by an estimation neural network to produce an estimate of the at least one excluded variable, and wherein the trained encoding neural network has been trained using an error metric inclusive of the difference between the at least one excluded variable and an estimate of the at least one excluded variable; and wherein, based upon the current estimate of functional capacity, one or more actions are performed, the one or more actions selected from the group consisting of:

the control circuit renders a display on a display screen of the current estimate in a time series with prior estimates to a clinician for review of possible health changes in the monitored human subject;

the control circuit compares the current estimate to prior estimates and testing for a change whereupon an electronic alert is triggered and transmitted to a clinician to investigate the health of the monitored human;

the control circuit compares the current estimate to prior estimates and testing for a change whereupon the control circuit transmits an electronic questionnaire to the monitored human subject;

the control circuit compares the current estimate to prior estimates and testing for a change whereupon the control circuit makes an entry in an electronic medical record of the monitored human subject indicating a change in health of the monitored human subject occurred;

the control circuit compares the current estimate to estimates from other monitored human subjects, in order to quantify health affects between at least a control group receiving a first intervention and a test group receiving a second intervention in a clinical trial; and the control circuit transmits an electronic control signal that controls the operation or sets a parameter of a medical device associated with treating or monitoring the monitored human subject.

11. The system of claim 10, wherein the trained encoding neural network is trained by application of training data to an encoding neural network, and the trained encoding neural network is produced in a plurality of iterations, and for each of the iterations and for each of a plurality of training human subjects, a first duration of training data comprising a substantially contiguous time series of the selected plurality of cardiopulmonary variables from a training human subject is input to the encoding neural network, a second duration of the training data, substantially non-overlapping in time with the first duration, comprising a substantially contiguous time series of the selected plurality of cardiopulmonary variables from the training human subject, provides input to an estimation neural network and wherein the estimation neural network provides the estimate of the at least one excluded variable.

12. The system of claim 10, wherein the functional capacity is VO2Max.

13. The system of claim 10, wherein the time series of selected plurality of cardiopulmonary variables is obtained by sensors that are non-invasively secured to the skin of the humans.

14. The system of claim 10, wherein the time series of selected plurality of cardiopulmonary variables is obtained by sensors and the sensors are selected from the group consisting of a camera, an electrocardiographic sensor, a light sensor, an accelerometer, an RF energy sensor, a temperature sensor, and a gyroscopic sensor.

15. The system of claim 10, wherein the functional capacity estimator generates the current estimate of the metric of functional capacity using one of: a linear regression technique, a decision tree, a random forest estimation, or a gradient boosting model.

16. The system of claim 10, wherein functional capacity estimator comprises an estimation neural network.

17. The system of claim 10, wherein the cardiopulmonary variables comprise one or more of: a heart rate, a measure of physical activity or motion, a time domain heart rate variability, a respiration rate, a tilt angle, an A-fib probability, and a sample time difference.

18. The system of claim 10, wherein the current cardio profile vector comprises a plurality of real numbers, each of the real numbers associated with one or more of the cardiopulmonary variables.

19. A method for treating and improving the cardiopulmonary health of humans, the method comprising:

receiving at an estimation neural network a time series of a subset of a selected plurality of cardiopulmonary variables, the subset omitting at least one excluded variable from the selected plurality of cardiopulmonary variables, and generating an estimate of the at least one excluded variable, wherein the estimation neural network is configured to use weights output by a function generator neural network as weights of connections between nodes in the estimation neural network;

iteratively training in tandem and by a plurality of iterations an encoding neural network to produce a trained encoding neural network and the function generator neural network to produce a trained function generator neural network, the training using an error metric inclusive of the difference between the at least one excluded variable and the estimate of the at least one excluded variable generated by the estimation neural network;

training a functional capacity estimator to produce a trained functional capacity estimator, wherein the function capacity estimator accepts as input a cardio profile vector generated by the trained encoding neural network, and outputs an estimate of a metric of functional capacity;

applying a duration of monitored data from a monitored human subject to the trained encoding neural network to produce a current cardio profile vector;

accepting as input to the trained function capacity estimator the current cardio profile vector generated by the trained encoding neural network, and outputting from the trained function capacity estimator an estimate of a metric of functional capacity;

based upon the current estimate of functional capacity, performing one or more actions selected from the group consisting of:

displaying the current estimate in a time series with prior estimates to a clinician for review of possible health changes in the monitored human subject;

comparing the current estimate to prior estimates and testing for a change whereupon an alert is triggered to a clinician to investigate the health of the monitored human;

comparing the current estimate to prior estimates and testing for a change whereupon a questionnaire is sent to the monitored human subject;

comparing the current estimate to prior estimates and testing for a change whereupon an entry is made in the medical record of the monitored human subject indicating a change in health of the monitored human subject occurred;

comparing the current estimate to estimates from other monitored human subjects, in order to quantify health affects between at least a control group receiving a first intervention and a test group receiving a second intervention in a clinical trial; and controlling the operation or setting a parameter of a medical device associated with treating or monitoring the monitored human subject.

20. The method of claim 19, wherein for each of the iterations in producing the trained encoding neural network and for each of a plurality of training human subjects, training data is used, wherein:
- a first duration of the training data comprises a substantially contiguous time series of the selected plurality of cardiopulmonary variables from a training human subject is input to the encoding neural network; and
- a second duration of the training data, substantially non-overlapping in time with the first duration, comprises a substantially contiguous time series of the selected plurality of cardiopulmonary variables from the training human subject, provides input to the estimation neural network and wherein the estimation neural network provides the estimate of the at least one excluded variable.

21. The method of claim 19 wherein the training of the function capacity estimator uses a plurality of matched examples to produce the trained functional capacity estimator, each of the matched examples comprising a cardio profile vector matched with a corresponding measured functional capacity metric of that person, to enable regression of an input of a cardio profile vector to an estimate of the metric of functional capacity.

22. The method of claim 19, wherein the functional capacity is VO2Max.

23. The method of claim 19, wherein the time series of selected plurality of cardiopulmonary variables is obtained by sensors that are non-invasively secured to the skin of the humans.

24. The method of claim 19, wherein the time series of selected plurality of cardiopulmonary variables is obtained by sensors and the sensors are selected from the group consisting of a camera, an electrocardiographic sensor, a light sensor, an accelerometer, an RF energy sensor, a temperature sensor, and a gyroscopic sensor.

25. The method of claim 19, wherein the functional capacity estimator generates the current estimate of the metric of functional capacity using one of: a linear regression technique, a decision tree, a random forest estimation, or a gradient boosting model.

26. The method of claim 19, wherein functional capacity estimator comprises an estimation neural network.

27. The method of claim 19, wherein the cardiopulmonary variables comprise one or more of: a heart rate, a measure of physical activity or motion, a time domain heart rate variability, a respiration rate, a tilt angle, an A-fib probability, and a sample time difference.

28. The method of claim 19, wherein the current cardio profile vector comprises a plurality of real numbers, each of the real numbers associated with one or more of the cardiopulmonary variables.

29. A system that is configured to treat and improve the cardiopulmonary health of humans, the system comprising:
- a sensor for obtaining a duration of monitored data from a monitored human subject, comprising substantially contiguous time series of a selected plurality of cardiopulmonary variables, the sensor being deployed with a monitored human subject;
- a control circuit, the control circuit coupled to the sensor, the control circuit being configured to:
  apply a time series of a subset of the selected plurality of cardiopulmonary variables to an estimation neural network, the subset omitting at least one excluded variable, and generating an estimate of the at least one excluded variable, wherein the estimation neural network is configured to use weights output by a function generator neural network as weights of connections between nodes in the estimation neural network;
  iteratively train in tandem and by a plurality of iterations an encoding neural network to produce a trained encoding neural network and the function generator neural network to produce a trained function generator neural network, the training using an error metric inclusive of the difference between the at least one excluded variable and the estimate of the at least one excluded variable generated by the estimation neural network;
  train a functional capacity estimator to produce a trained functional capacity estimator, wherein the function capacity estimator accepts as input a cardio profile vector generated by the trained encoding neural network, and outputs an estimate of a metric of functional capacity;
  apply a duration of monitored data from a monitored human subject to the trained encoding neural network to produce a current cardio profile vector;
  wherein the trained function capacity estimator accepts as input the current cardio profile vector generated by the trained encoding neural network, and the trained function capacity estimator outputs an estimate of a metric of functional capacity;
- based upon the current estimate of functional capacity, perform one or more actions selected from the group consisting of:
  display the current estimate in a time series with prior estimates to a clinician for review of possible health changes in the monitored human subject;
  compare the current estimate to prior estimates and testing for a change whereupon an alert is triggered to a clinician to investigate the health of the monitored human;
  compare the current estimate to prior estimates and testing for a change whereupon a questionnaire is sent to the monitored human subject;
  compare the current estimate to prior estimates and testing for a change whereupon an entry is made in the medical record of the monitored human subject indicating a change in health of the monitored human subject occurred;
  compare the current estimate to estimates from other monitored human subjects, in order to quantify health affects between at least a control group receiving a first intervention and a test group receiving a second intervention in a clinical trial; and
  control the operation or setting a parameter of a medical device associated with treating or monitoring the monitored human subject.

30. The system of claim 29, wherein for each of the iterations in producing the trained encoding neural network and for each of a plurality of training human subjects, training data is used, wherein:
- a first duration of the training data comprises a substantially contiguous time series of the selected plurality of cardiopulmonary variables from a training human subject is input to the encoding neural network; and
- a second duration of the training data, substantially non-overlapping in time with the first duration, comprises a substantially contiguous time series of the selected plurality of cardiopulmonary variables from the training human subject, provides input to the estimation neural network and wherein the estimation neural network provides the estimate of the at least one excluded variable.

31. The system of claim 29 wherein the training of the function capacity estimator uses a plurality of matched examples to produce the trained functional capacity estimator, each of the matched examples comprising a cardio profile vector matched with a corresponding measured functional capacity metric of that person, to enable regression of an input of a cardio profile vector to an estimate of the metric of functional capacity.

32. The system of claim 29, wherein the functional capacity is VO2Max.

33. The system of claim 29, wherein the time series of selected plurality of cardiopulmonary variables is obtained by sensors that are non-invasively secured to the skin of the humans.

34. The system of claim 29, wherein the time series of selected plurality of cardiopulmonary variables is obtained by sensors and the sensors are selected from the group consisting of: a camera, an electrocardiographic sensor, a light sensor, an accelerometer, an RF energy sensor, a temperature sensor, and a gyroscopic sensor.

35. The system of claim 29, wherein the functional capacity estimator generates the current estimate of the metric of functional capacity using one of: a linear regression technique, a decision tree, a random forest estimation, or a gradient boosting model.

36. The system of claim 29, wherein functional capacity estimator comprises an estimation neural network.

37. The system of claim 29, wherein the cardiopulmonary variables comprise one or more of: a heart rate, a measure of physical activity or motion, a time domain heart rate variability, a respiration rate, a tilt angle, an A-fib probability, and a sample time difference.

38. The system of claim 29, wherein the current cardio profile vector comprises a plurality of real numbers, each of the real numbers associated with one or more of the cardiopulmonary variables.

* * * * *